United States Patent [19]

Chiang

[11] Patent Number: 5,663,483

[45] Date of Patent: Sep. 2, 1997

[54] TRANSGENIC MICE EXPRESSING HUMAN CHOLESTEROL 7αHYDROXYLASE

[75] Inventor: John Young Ling Chiang, Stow, Ohio

[73] Assignee: Northeastern Ohio Universities College of Medicine, Rootstown, Ohio

[21] Appl. No.: 361,458

[22] Filed: Dec. 21, 1994

Related U.S. Application Data

[63] Continuation of Ser. No. 135,488, Oct. 13, 1993, abandoned.
[51] Int. Cl.$^6$ ............................. C12N 5/00; C12N 15/00
[52] U.S. Cl. ................... 800/2; 800/DIG. 1; 435/172.3; 435/354
[58] Field of Search ............................... 800/2, DIG. 1; 424/9; 536/23.1, 23.5, 24.1, 23.2; 435/172.3, 320.1, 240.2

[56] References Cited

PUBLICATIONS

Lusis, Aldons J., "The Mouse Model for Atherosclerosis", TCM 3(4): 135–143 (1993).
Dueland, Svein et al., "Effect of Dietary Cholesterol and Taurocholate on Cholesterol 7α–hydroxylase and Hepatic LDL Receptors in Inbred Mice", Journal of Lipid Research 34: 923–931 (1993).
Dueland, Svein et al., "Expression of 7α–Hydroxylase in Non–hepatic Cell Results in Liver Phenotypic Resistance of the Low Density Lipoprotein Receptor to Cholesterol Repression", Journal of Biological Chemistry 267(32): 22695–22698 (1992).
Watson et al (1987) Molecular Biology of the Gene, p. 313.
Nishimoto et al. (1993) Biochemica et Biophysica Acta 1172:147–150.
Merlino (1991) FASEB J 5: 2996–3001.
Ness et al. "Effect of Thyroid Hormone on Hepatic Cholesterol 7αHydroxylase, LDL Receptor, HMG–CoA Reductase, Farnesyl Pyrophosphate Synthetase and Apolipoprotein A–I mRNA Levels in Hypophysectomized Rats", Biochem. and Biophy. Res. Comm., 172(3):1150–1156, (1990).
G Ciliberto et al (1987) EMBO J, 6: 4017–4022.
JW Gordon et al (1981) Science 214:1244–1246.
RL Brinster et al (1988) Proc Natl Acad Sci USA 85:836–840.
Karam, W. G. et al., "Polymorphisms of Human Cholesterol 7α–Hydroxylase", Biochem. and Biophys. Res. Comm. 185(2):588–595 (1992).
Breslow, J. L. et al., "Transgenic Mouse Models of Lipoprotein Metabolism and Atherosclerosis", Proc. Natl. Acad. Sci. USA 90: 8314–8318 (1993).
Cohen, J. C. et al., "Cloning of the Human Cholesterol 7α–Hydroxylase Gene (CYP7) and Localization to Chromosome 8q11–q12", Genomics 14: 153–161 (1992).
Nishimoto, M. et al., "Structure of the Gene Encoding Human Liver Cholesterol 7α–Hydroxylase", Biochimica. et Biophysica. Acta. 1172: 147–150 (1992).
Thompson, J. F. et al., "Cholesterol 7α–Hydroxylase Promoter Separated from Cyclophilin Pseudogene By Alu Sequence", Biochimica et Biophysica Acta 1168: 239–242 (1993).

(List continued on next page.)

Primary Examiner—Bruce R. Campell
Attorney, Agent, or Firm—Foley & Lardner

[57] ABSTRACT

Genomic DNA of cholesterol 7α-hydroxylase and a minigene are disclosed. The minigene is used for making a transgenic animal that produces functionally active cholesterol 7α-hydroxylase and functions as a disease model. A cholesterol 7α-hydroxylase promoter region and reporter gene construct is provided, as well as a transgenic animal that expresses the promoter/reporter gene.

10 Claims, 8 Drawing Sheets

PUBLICATIONS

Li, Y. C. et al., "The Expression of a Catalytically Active Cholesterol 7α–Hydroxylase Cytochrome P450 in *Escherichia coli*", *The Journal of Biological Chemistry* 266(29): 19186–19191 (1991).

Molowa, D. T. et al., "Transcriptional Regulation of the Human Cholesterol 7α–Hydroxylase Gene", *Biocemistry* 31: 2539–2544 (1992).

Nishimoto, M. et al., "Structural Analysis of the Gene Encoding Rat Cholesterol α–Hydroxylase, The Key Enzyme for Bile ...", *The Journal of Biological Chemistry* 266(10): 6467–6471 (1991).

Jelinek, D. F. et al., "Structure of the Rat Gene Encoding Cholesterol 7α–Hydroxylase", *Biochemistry* 29(34): 7781–7785 (1990).

Chiang, J. Y. L. et al., "Cloning and 5'–Flanking Sequence of a Rat Cholesterol 7α–Hydroxylase", *Biochimica et Biophysica Acta* 1132: 337–339 (1992).

FIG. 3

Molecular-weight 57658  #Length 505  #Checksum 7470

```
  1 MMTTSLIWG IAIAACCLWL ILGIRRRQTG
 31 EPPLENGLIP YLGCALQFGA NPLEFLRANQ
 61 RKHGHVFTCK LMGKYVHFIT NPLSYHKVLC
 91 HGKYFDWKKF HFATSAKAFG HRSIDPMDGN
121 TTENINDTFI KTLQGHALNS LTESMMENLQ
151 RIMRPPVSSN KTAAWVTEGM YSFCYRVMP
181 EAGYLTIFGR DLTRRDTQKA HILNNLDNFK
211 QPDKVPPALV AGLPIHMPRT AHNAREKLAE
241 SLRHENLQKR ESISELISLR MFLNDTLSTP
271 DDLEKARTHL VVLWASQANT IPATPWSLFQ
301 MIRNPEAMKA ATEEVKRTLE NAGQKVSLEG
331 NPICLSQAEL NDLPVLDSHI KESLRLSSAS
361 LNIRTAKEDF TLHLEDGSYN IRKDDIIALY
391 PQLMHLDPBI YPDPLTFKYD RYLDENGKTK
421 TTFYCNGLKL KYYYMPFGSG ATICPGRLPA
451 IHEIKQFLIL MSYFELELIE GQAKCPPLD
481 QSRAGLGILP PLNDIEFKYK FKHL*
```

FIG. 4A

```
   1 TTTTTGGTTA TCTTTTCAGC CGTGCCCCAC TCTACTGGTA CCAGTTTACT GTATTAGTCG
  61 ATTTTCATGC TGCTGATAAA GACATACCTG AAACTGGACA ATTTACAAAA GAAAGAGGTT
 121 TATTGGACTT ACAATTCTAC ATCACTTGGG AGGCCTCACA ATCATGATGG AAGGAGAAAG
 181 GCACATCTCA CATGGCAGCA GACAAGAAAA GAGCTTGTGC AGGGAAACTC CTCTTTTTAA
 241 AACCATCAGA TCTCATGAAA TTTATTCATT ATCATGACAA TAGCACAGGA AAGAACTGCA
 301 CCCATAATTC AGTCACCTCC TACCAGGTTC CTCCCACAAC ACGTGAGAAT TCAAGATGAG
 361 ATTTGGATGG GGACACAGCC AAACCATGTC ACACTACCAT GCCTGACTTC CTTTCCATTT
 421 TTGTATATTT GCTTGTTCTT CATTTGCCCG AGAAGTAACT CTAAAGGGCT GTATTATTTG
 481 GATATTAGAT TGGCATTTTA TCTGACTGGG ATATCTTGCT GTGATTGTCC ATGTATAAGA
 541 TCAGCTTTTC TATAAGCCAT ATTTTTAAAA AGATATATTA ATTTTTTAAA AATCCACCTG
 601 TCTAAATAAA TGCACAAAGC CCCCCAAAAA CCTAGATTCT AAGAAAAATC TATGTACTGC
 661 CATACAATGA TTGATATTAA TATTTATGGT GATAAATTAC ACACAAAAAA TGTGTGATCT
 721 CTGTTTAAAC AGGCAAAAAC AAAAAACACA TGAAATAAAT CTATGGCATC TATAGCCAAA
 781 ACTGGAAACA ACCCACATAT CCATCAATAG GAAATCAGTT AAATAAATTA TAGTACATTT
 841 ATCCAATGGA AGATTAAGCA CATATTCAAT ATAATTATTT ATACACACAT ATAGATACAC
 901 ACATGTATAA ATATAGAGAA TACTGTGGGT GTATGTGTGT GTGTTTAT ATACATATAT
 961 ATACACACAC AGTACTGTTG CCTACCTTCT TTTGTCTTAA TTCTGTGAAC TCTCATTCAC
1021 TCTGCTTCAG TAGGATACCT CCTTCTTTTT GGTTCTTAGA CTCACCAAGT TGATCCTTGA
1081 CTCAAGACAT TGCATTTGCT GCTTCCTCTT CCTGGAATAT CCTTCCTTCT GATATTCACA
1141 TGAGTAGTCT CTTCTTGTCA TTCAGATCTC AAATGTCACA ATTTCAGAGA GCCCATCTCT
1201 GATCATCATA TCTAAAGTTG TCCTCATTCC CCCATAGCTT TCTATACCAT GTTTTATTTT
1261 TTTCATAACA TGTATTTTAT TACTCCTTTC TCCATTGGAA TAGAATCTCC ATTAGATTAG
1321 GAAATCTGCC TATCTTATTA ATGCCTGCAA CTGGAATACT TTTGAAGAGT TCTTGGCACG
1381 TAATAAATAC TCAACTAATA TTTTTGTGTA CACAGAAATA AAGTTTGGAA GAACAGATGC
1441 CAAATTGTTA CTAGTGGTTA CTTCTGAGTA AAGGAGTAGC ATGGTAGGTA AATTATTAAT
1501 AGATGTTCAC TTTCCACCAA GATATGTTTT AGTTAGTCTT AACTTACTTG AAATGAAATT
1561 TATTACTTTA ATAATTAGAA ACATTGATAA ACATTTTAGT CACAAGAATG ATAGATAAAA
1621 TTTTGATGCT TCCAATAAGT TATATTTATC TAGAGGATGC ACTTATGTAG AATACTCTCT
1681 TGAGGATGTT AGGTGAGTAA CATGTTACTA TATGTAGTAA AATATCTATG ATTTTATAAA
1741 AGCACTGAAA CATGAAGCAG CAGAAATGTT TTTCCCAGTT CTCTTTCCTC TGAACTTGAT
1801 CACCGTCTCT CTGGCAAAGC ACCTAAATTA ATTCTTCTTT AAAAGTTAAC AAGACCAAAT
1861 TATAAGCTTG ATGAATAACT CATTCTTATC TTTCTTTAAA TGATTATAGT TTATGTATTT
1921 ATTAGCTATG CCCATCTTAA ACAGGTTTAT TTGTTCTTTT TACACATACC AAACTCTTAA
1981 TATTAGCTGT TGTCCCCAGG TCCGAATGTT AAGTCAACAT ATATTTGAGA GACCTTCAAC
2041 TTATCAAGTA TTGCAGGTCT CTGATTGCTT TGGAACCACT TCTGATACCT GTGGACTTAG
2101 TTCAAGGCCA GTTACTACCA CTTTTTTTTT TCTAATAGAA TGAACAAATG GCTAATTGTT
2161 TGCTTTGTCA ACCAAGCTCA AGTTAATGGA TCTGGATACT ATGTATATAA AAAGCCTAGC
2221 TTGAGTCTCT TTTCAGTGGC ATCCTTCCCT TTCTAATCAG AGATTTTCTT CCTCAGAGAT
2281 TTTGGCCTAG ATTTGCAAAA TGATGACCAC ATCTTTGATT TGGGGGATTG CTATAGCAGC
2341 ATGCTGTTGT CTATGGCTTA TTCTTGGAAT TAGGAGAAGG TAAGTAATGT TTTATCTTTA
2401 AATTGCTCTT TGATTCATCC ATTTAATTTT TTTACCTTCA TTTTTATACA GTAAATTTGG
2461 TTTTCTATAC TTACACATAT TAGCATTATC TTCCTTATGT TTTAAATGAA AAATTTGATT
2521 TGAATTTTTA AAGTAATATC TTTTTTACTA TATCTCACAA GACATATGAC AGCTTCCCTT
2581 TTTAGTATTG GCATATACCG ATGGTAATAT ATAAATGTAT ATTGGTGTTA AACATAACTG
2641 ACAGAAATTG TATAAGGTCT CTATGTACAT TTATATGTGT ATCTAAAGAG GAAGCCCAGA
2701 TTAGTAAGGA TACAAGTAGC AAGTGGGAAT CTACAATGGA AAGGATTGCT TTCTCTCACA
2761 TGGCTTCAAT AGATACTCTT GCTTAAATAA ATGTTCTCTT TTAAGCTCAT TCTTGTGCAT
2821 CGCATAGACT CAGCCTAAGC CTGAACAAGA GCATAGAGCC TGAGCTGATC ATTCTATTAC
2881 TGTTTTTAAA TAAATGTTAA TCAACTGTGG TGAATTGGGA AAGTTTGCTG AGTGTATGTG
2941 ACATCGATTT CATTTATTTA CAACTGGTTC AAGAATGCAA GAAAACAAA TACAGTCAGA
3001 TCCAGAACCA TAGTTTATTT AACTTCTAAT TGGCTCAAGG AGTAATTGTG GGGAGGCATA
3061 TAGATATTCT CTGCTATGTC AATCTCAAAA AGAGAAAATA ACCCTAACCA TCTTTCAGCT
3121 TTGTAGATTG CTATGTGTTT CTGCCTTTG CAGTTTCTTT CAGGCCTGAT AGTTTTTACT
3181 TTTAATTAAA CTACTTATCT TCAAACTAAG AAAAGAAAGG TAATTACTTT ATACTGTATT
3241 ATTCTATCAA GAGGTACAGA AGTTTATGTT GGAAAATAAG TTTACATGTT CTAATAAAAA
3301 CATTTTAAAG GAGCACTGAA TTACAATAGA TGATTCCGTC AGTGTTTATC TTACTCAATT
3361 TCATTTTATA ATAAGCTGAT TTCTCACATG AGATTCTTCT TCTCTGAAAC CATCCTTATA
3421 GAATATAATA TAGATATCTT TAAACTAGGA ATATTTTCAA AACCTCAGTT CTGAAATCCT
```

FIG. 4B

```
3481 CCCTTATTCA GTGATCTGTG TCTTTAAAGA AAATAATCAA AAGAAACATT TTGAGATATT
3541 TAGAAAAATG ATGCTTAGCA AAGTGATAAA CACTAGAATG TAGTTTTGTT TCCGCACTGA
3601 CAACAAGAAT CTTGTTGGTC TTGTAAATCC TTTTGCCTGT ATCACTGGGA AAAGTGATGA
3661 GCACATAGTA GACGGGTGCT TGTTGAATGT GTATATGGAC GGATGCATGA ATGGATGGAT
3721 TTAGTAATCC TTTCCACCAA CATATCATGT TACTAGGTTA ATATAACCTA TTACTGTAGT
3781 AAAAGAGCAG GGCCCATCCA ACAAAAGAAA TATCTATAAA CTATAGGGTT TCAAAGTTTG
3841 AAGTCAGTGG GAAAAATTTT AAAACCTGAT GTAAGTAAAA ACCCAAAACT GTAATCATCC
3901 ATGTCTATCA TACACTTGTG TCTGACAGGC AAACGGGTGA ACCACCTCTA GAGAATGGAT
3961 TAATTCCATA CCTGGGCTGT GCTCTGCAAT TTGGTGCCAA TCCTCTTGAG TTCCTCAGAG
4021 CAAATCAAAG GAAACATGGT CATGTTTTTA CCTGCAAACT AATGGGAAAA TATGTCCATT
4081 TCATCACAAA TCCCTTGTCA TACCATAAGG TGTTGTGCCA CGGAAAATAT TTTGATTGGA
4141 AAAAATTTCA CTTTGCTACT TCTGCGAAGG TAAGCAGTTT TACATTTATA TACCATTCTG
4201 TTTGTCTTCT ACCTTTTTAT GTGCTTGTCT ATTTAGAAAT TTTGATGTAC TTAGATTTTA
4261 TGATAAAGGT GTTGAAGAGA GTTATCCTTA TGTGGAGATT CTTAGAAACA TAAATAAATT
4321 ATACGTAGCT TCTTAGTAAT AATCATTTAG AAAGTCAAAA TAGGTATAGA TTTCCGTCAT
4381 TTGCTTTGCA CGAGCTAATG AGGGTGAAAT ACAGATTAAA TGCTCTACTG AGACAGGTGG
4441 CACTGTACGA ATAAGATAGA TTAAAATTCA TCACATCAGC AATGTCTATG CAGAGCGAAG
4501 TGACGGAAAC CTAACATTCA GCAGTTGTCT CACCACACTT GTGCCACACA GTGTTTCATT
4561 TTGATAAGGA ATTGGCAAGA TATTTTAACA TCATTTAGAT GTAATAAAAG AAGATCTGTT
4621 ACTGAGAAAA AAAACCAATA ACTACTTACT TACTGCAAAT AAATATTAGC TTTGGTCTTT
4681 GTGACTAAGT AGCTTAAAGT TTGGTTAAAA TACATCTACA GCTGGACACA ATGGAACACA
4741 CCTGTAGTCC CTGCTATTTG AGAGGCTGAG GCAGGAGGAT CGCTTGAGTC CAGGAGTTTG
4801 AGGCTGCAGT GAGCTATCAT TGTGTCACTG CACTCCAGCC TGGGTGACAA TGTGAGACCC
4861 CATCTCTAAA AGAAAAAGAA AAAGAAATCT ACAAATAATA TAAAAGATAA CTAATGATTT
4921 TAAAACATTA TCAATTAGTT TATGTGCAAT AGCTGTAAAT AAGTGCAGTA GCATAAGAAA
4981 TAAGACATAG ATGACTTGAG TGATCCAGGG GAGTGCCACT GAAGTTGGCT TTAAAGGAAA
5041 GGTACAGTTT GGTCATTTAT TTGTAAAGTG CTATGAACTT GTACAAGGGA AAGCCAATTT
5101 CCCGTGTTTA CCAAGTAAGG AACTATGAAA GTATCTAATC CGTTTTTCAG TCATTTACTA
5161 TGACTAGGTC AGGTTTAACT TCTTTTTCTG CATGTTTTAT TTGCTATCAG GCATTTGGGC
5221 ACAGAAGCAT TGACCCGATG GATGGAAATA CCACTGAAAA CATAAACGAC ACTTTCATCA
5281 AAACCCTGCA GGGCCATGCC TTGAATTCCC TCACGGAAAG CATGATGGAA AACCTCCAAC
5341 GTATCATGAG ACCTCCAGTC TCCTCTAACT CAAAGACCGC TGCCTGGGTG ACAGAAGGGA
5401 TGTATTCTTT CTGCTACCGA GTGATGTTTG AAGCTGGGTA TTTAACTATC TTTGGCAGAG
5461 ATCTTACAAG GCGGGACACA CAGAAAGCAC ATATTCTAAA CAATCTTGAC AACTTCAAGC
5521 AATTCGACAA AGTCTTT
```

FIG. 5

```
   1 GAATTCTACT CTTTAAAGGG GTGAATATTA TGGTACTTGA ATTTTATCTC AAGAAAAATG
  61 AATAAAAAGT AACTAAATCA TTGAAAATAT CTGATGGCAT GGGGTTTGTG GGGTAACTGG
 121 CATTCCACAG TGATTTTCAA AGGGCTTGTG CTGTTTTCAT TTTGCTTTGT TTTAGTTATG
 181 GAGCCCTTCC TTGAAACAAA CTTCATACTA CAGTCCTCTT TCATGAAGCA GAAGAGGGCA
 241 GTGGGCAGAG CTCTCCTTTG GCTTTCTCCC CCACCACAAC AGGGAGCCCT GGAGCTCTAG
 301 GAGAGAAAAT CTGAAATATA AAGGGCATGC ATGTGAGCTG TGGAGTCCCA GAGCCCTGGG
 361 TTTGCATCCT AGATCTGCAA CTCCCGTGAA TTGAGTTTTG GAAGTTGCT GAAACTCTGA
 421 CCTCCTGTTT TCTCATGGTA TTGTTGTAAG GGTTAAATGA GACAATGTAT GTGAAGACCC
 481 TGGCCCCACA GTAGAGGCTC TGCACACATT TCAGCGATAC TTTCCTCATG TATTTCCAAA
 541 AATGTTTTCT CATTTTCTTA AAATGTCAGA AAGAAGACAA CAGAACTTAC TTGCCTTTTA
 601 CAACAGAACA AATGGAGCAA GTCAGAGGTC AAGGTGCTAA CATTCTTCAT GGTTCCTCAC
 661 CACCTTTTGT TCTGTTAGCC TATAGGGAAA AGTCTTCTTT CTCATCTCAT TATCTGCAGG
 721 GGAAAATAGT ACTTCAGCAA GTGATCCAGT TGAAGAACAT CTCCAGGGCC ATTAACATAC
 781 AGAGGTTTGT TCTACTCTCT CTGTGCTCCA TGTCTAAGAA CCTCAGCCTT CCTCCTAGGA
 841 GCTAGGGAAA GTCAGGAAAG TGAAATAGT ACCCCAGCTA ATGAACTGCC CTGTGCTGGC
 901 CTGAGAAGAC AAGACCAGCT TCCTCAATGG CTCAAGATTT GGTTTCCTTC AATATGTCCT
 961 TTTGGAAATA TGTCCATGAC ATCGGAGAGA TAAAAGGAGC CAGGATTGCT CACATTCAGG
1021 AAAAAAGCTC CACTATCTTT CTCTCTCTCC CTCTTTCTCT CCCTCCCCCT GACTGCCCTC
1081 TTCTCTATCT CTCTCTCTCC CTGAGCTGGC AAGGTTAATT GGTCGCAGAA AGCCGAAGAA
1141 ACAAGTGGGC CTCCTGGAAC AAAGTTCAAA AAGCCGAAAA CGGGAAGAAA ACTAACCACA
1201 AAAGTAAAGG AACCACTTAG CCTTCTTTGA TTCCAGGCCC CCAAGCCTGT CTTTAACTTG
1261 GATGAATGGA GTTCTTCCTG TGCTACAGCA CCGCATAGTA GGGGCTGCCC TGGGCCTGAA
1321 GCCAGAGCTT CACCATATTC AGTCATCTGT ACATTGAGGC AACAGTGCCT GCTTCATGGT
1381 GCTACCCTGT GGATTAAATG AAGCAAGTTT TTGATGATCT TGACACTGAA TATTGATGCA
1441 TTGGTCAGAC TTTTTCTGAT AGTAAAAAAT GGTGGTTTCT TGTTGTCAGA AATCAAATCA
1501 ATATATTTGT TCTCCTGTTG ATTAGCTATG TCCCCTAGAG GGCAGCGACT TTGCCTGTCT
1561 TATTTATCTC TGCATCTCCA GCACTTAAAA GGTGCCTTGC ATAAGGTACA TATTAAGTTC
1621 ATATGAATGA ATGAATGAAA TGCATATGAT TTATTCATAC CCAGTTGGTG GTGTGTTTAC
1681 CCTTTCCTAA ACCTGTAGTC AGATGGCCTT TGAATCCCCT GTACTTCTTG TGAGGTACTG
1741 TGCTGTAAAG GTGGACTATC ACACTTCAGT TCAGAGCAAT CTGGGCTTGA ATCCTGGATT
1801 TGCCAGTTTA TTAACTATAG CAAACATTTT TGAGCATACA TTGTGCCAAG TGCTAGGCTA
1861 ACTGTCTTAC ACACATTGTC TTATTTCGTC TTAATATCTA TGAGTCATGC ACTATAATCA
1921 TCCCCATTTT ACAGATAAGA AAGCAAAGAC TTGGAGAGGA AAAGCATCTT GTTCAAAGGT
1981 AAATACTTAA TGGCCAAGCC AACATGCAAA TCTAGATTTA ATTGCAGCTT CCTCTTCATC
2041 TACCATTCGA ACTAATTCAA GCTATGTAAT ATTTCCCACT GAACCTTCTT GCCTCTACTT
2101 CCTCATCTTT AACATGGTCA AAATACCTGT CCTGCCCAAG TTAGTTATTT CATTAAAGTA
2161 GAAAATACA AGAGAAGCTT TTAAAATGTG AAACCTCAAA TGAATGTAAA ATTATGATGA
2221 TTCCTTTAGA ATTTGTCAAC ACCTTCTTTT CTCTACTCCT GCTAGGCATT TACAATCTCA
2281 AAACCATGTA TTTAAGATGC AAAACTATAT TTGTATTTGC CATAACTGGT TTCTTTCCCT
2341 ATGGCTTCAT GAAAATGTGG CTCGAATGTG TTTATTATGA AAGCCCAAA TTAATCACGA
2401 CAAGACTTCA CCAGCCCATT CCACAATAGA CTCCCATTAC TTTGCCCTGA CTTAGAAACC
2461 TCATATACAG TCTTGATTCA GTACAGCTCT GTGATGCTCT TGGAAAATGC AAAGTGCTTT
2521 CTTAATTGAG GCAATCTGTG TCCCACTACA GAGAGGTGGT TTAACTTGTG AATTC
```

FIG. 6

```
   1 AGAGCAACCT GGGCAACATA GCAAAACCCT GTCTCTGCAA ACAATAAAAA GAAGAAAATT
  61 AGCTGGGTAT GGTGGCACAT GCTATAGTCG CAGCTACTCG AGAGGTTGAG GTGGGAGGAT
 121 CAGTTCAGCC TGGGAGGTTG AGGCTGCAGT GAGCCAGATC ATGCCACTGC ACTGCAGCAT
 181 GGGCAACAGA ATGAGACCCT GGCTAAAAGA AAACAAAATA AAAAATTCAG ACACAGGTTG
 241 AATCATTGAT AACAGCATAG TGGTAACAGA AAGAAAGTTT GGGAAATTTT TATCTGATCA
 301 GCTTCCCATA CCCTGTTCAT CTTTGTGTTA TGCACTGCCA GGCTGTCTGT AGGTTCAGAC
 361 TCTATATCAT ATGACCTTCA AACACTTGGT TTGTTCTTCT CCTTCCTTCC TCCCTTCTTC
 421 TTTCATTTTT TATCTTTTTT TCTTTTAAAA TGTTTAGATA GTATAATAAG GAACTGCTGA
 481 GGCTTTCCAG TGCCTCCCTC AACATCCGGA CAGCTAAGGA GGATTTCACT TTGCACCTTG
 541 AGGACGGTTC CTACAACATC CGAAAAGATG ACATCATAGC TCTTTACCCA CAGTTAATGC
 601 ACTTAGATCC AGAAATCTAC CCAGACCCTT TGGTAAAGTC GCAGTGTGCC CGAATTGAAA
 661 TTCAATATCC AGGTGATAGC TACCTAGATC TAAATAAAGA GGAAATTTAC AATGGTAGAA
 721 TTGATTTTCT CATAGTAGTC ACAGGAATTG TCTGACTTAA TTGTGTTAAA TATTCATATA
 781 TTTTGGAAAA TTTAGATAGT GGTCTGAATT TTTCATTTTA GTCCTGATAT TTGCCATCAC
 841 ACAGTCTTTG CTAGATTATA TTTGCAGTCA TGATAATAAA CCTGCCACTT TTTTTTTCTT
 901 AAAAAGCACC TCCTCCCAAA TCCAGGAAAT TGGAGGCTAA TATATTGATT ATTCTAGTTT
 961 CTTCTGGGAA CCCTTCTCTC TCTAGCTCTG CCTGACTAAG GAACTAATCG TTCAAGCAGG
1021 ATAGGAAGGT ATCACAAGGC TTCCTTAGCT GCATTAAGCT CCTGTTCCTT ATTACTTTCT
1081 GATTCAATGT GGAGTATTTG CTAAATCACT AATGGGGTAG AATTAAAAAG AAAATTACTC
1141 TTTGGAGCTT CCAGGTTTAG AAAGAGATAA ATTTCTTTAA AACTAGCTTA AAGGCGGTTT
1201 TCTTTGTATT TTTATTGCAG ACTTTTAAAT ATGATAGGTA TCTTGATGAA AACGGGAAGA
1261 CAAAGACTAC CTTCTATTGT AATGGACTCA AGTTAAAGTA TTACTACATG CCCTTTGGAT
1321 CGGGAGCTAC AATATGTCCT GGAAGATTGT TCGCTATCCA CGAAATCAAG CAATTTTTGA
1381 TTCTGATGCT TTCTTATTTT GAATTGGAGC TTATAGAGGG CCAAGCTAAA TGTCCACCTT
1441 TGGACCAGTC CCGGGCAGGC TTGGGCATTT TGCCGCCATT GAATGATATT GAATTTAAAT
1501 ATAAATTCAA GCATTTGTGA ATACATGGCT GGAATAAGAG GACACTAGAT ATTACAGGAC
1561 TGCAGAACAC CCTCACCACA CAGTCCCTTT GGACAAATGC ATTTAGTGGT GGCACCACAC
1621 AGTCCCTTTG GACAAATGCA TTTAGTGGTG GTAGAAATGA TTCACCAGGT CCAATGTTGT
1681 TCACCAGTGC TTGCTTGTGA AATCTTAACA TTTTGGTGAC AGTTTCCAGA TGCTATCACA
1741 GACTCTGCTA GTGAAAAGAA CTAGTTTCTA GGAGCACAAT AATTTGTTTT CATTTGTATA
1801 AGTCCATGAA TGTTCATATA GCCAGGGATT GAAGTTTATT ATTTTCAAAG GAAAACACCT
1861 TTATTTTATT TTTTTTCAAA ATGAAGATAC ACATTACAGC CAGGTGTGGT AGCAGGCACC
1921 TGTAGTCTTA GCTACTCGAG AGGCCAAAGA AGGAGGATGC TTGAGCCCAG GAGTTCAAGA
1981 CCAGCCTGGA CAGCTTAGTG AGATCCCGTC TCCAAAGAAA AGATATGTAT TCTAATTGGC
2041 AGATTGTTTT TTCCTAAGGA AACTGCTTTA TTTTTATAAA ACTGCCTGAC AATTATGAAA
2101 AAATGTTCAA ATTCACGTTC TAGTGAAACT GCATTATTTG TTGACTAGAT GGTGGGTTC
2161 TTCGGGTGTG ATCATATATC ATAAAGGATA TTTCAAATGT TATGATTAGT TATGTCTTTT
2221 AATAAAAAGG AAATATTTTT CAACTTCTTC TATATCCAAA ATTCAGGGCT TTAAACATGA
2281 TTATCTTGAT TTCCCAAAAA CACTAAAGGT GGTTT
```

TRANSGENIC MICE EXPRESSING HUMAN CHOLESTEROL 7α HYDROXYLASE

CROSS REFERENCE TO RELATED APPLICATIONS

This application is a continuation of application Ser. No. 08/135,488, filed Oct. 13, 1993, abandoned.

Work related to subject matter described in this application was provided by research supported in part by NIH Grant GM 31584.

Ser. No. 08/135,510, U.S. Pat. No. 5,420,028 (Attorney Docket No. 18748/176 "TRUNCATED HUMAN CHOLESTEROL 7α-HYDROXYLASE, METHOD OF PRODUCTION AND USE THEREOF" to Chiang, J.; and U.S. Ser. No. 08/135,511, U.S. Pat. No. 5,558,999 (Attorney Docket No. 18748/175) "CHOLESTEROL 7α-HYDROXYLASE GENE REGULATORY ELEMENTS AND METHODS FOR USING THEM" to Chiang, J. are both filed concurrently herewith and incorporated by reference in their entirety.

BACKGROUND OF THE INVENTION

High serum cholesterol is commonly associated with an increased risk of heart attack, atherosclerosis and circulatory disorders. In addition, a variety of diseases are caused by disorders of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7), commits cholesterol to bile acid synthesis and catalyzes the first and rate-limiting step of bile acid synthesis in the liver. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamins, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein.

The feedback of bile into the liver is known to inhibit cholesterol 7α-hydroxylase and thus inhibit the overall rate of bile acid synthesis. Cholesterol 7α-hydroxylase therefore has been a subject of intense investigations to elucidate the regulatory mechanisms of bile acid synthesis in the liver.

It is known that an interruption of bile acid reabsorption, such as that caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids, cholesterol, hormones, diurnal rhythm and other factors.

Generally, the regulation of eukaryotic genes is thought to occur at several locations, including the promoter sequences, which are located upstream of the transcription start site; enhancer or repressor sequences, which are located upstream of the promoter; within intron sequences, which are non-coding sequences located between exons or coding sequence; and in 3' sequences, which are located downstream from the coding region. The promoter sequence is unique to each gene and is required for the accurate and efficient initiation of gene transcription. Enhancers and/or repressors regulate promoter activity and determine the level of gene transcription during the development and differentiation of a particular tissue.

The promoter of most eukaryotic genes contains a canonical TATA box that binds a TFIID TATA box binding protein. TFIID complex and associated transcription activators (TAFs) interact with the basal initiation factors and RNA polymerase II to activate the promoter. The transcription complex assembly and initiation are regulated by transcription factors bound to enhancer elements located in the promoter and other regions of the gene (Pugh and Tjian, J. Biol. Chem. 267, 679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase gene expression at the molecular level are not understood. An understanding of the regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct coding, non-coding and promoter region gene sequences. An elucidation of the enzyme's gene structure, a method for analyzing promoter and enhancer/repressor activity, as well as transgenic animal models with which to study human cholesterol 7α-hydroxylase, are desired. Attempts to provide a transgenic animal expressing recombinant CYP7 have not been successful using the cDNA of CYP7. Thus, important discoveries concerning the CYP7 gene and systems for studying the CYP7 enzyme's physiology, each of which aims towards the design of therapeutic drugs and the treatment of patients with defects in bile acid synthesis and cholesterol metabolism, are highly desired.

SUMMARY OF THE INVENTION

Thus, an embodiment of the invention provides genomic DNA of cholesterol 7α-hydroxylase, in particular, DNA sequences of FIGS. 4, 5, and 6 (SEQ. ID NOS 4, 5 and 6, respectively), clones λHG7α26 (ATCC 75534) and λHG7α5 (ATCC 75535), and fragments thereof.

Another embodiment provides an expression vector comprising genomic DNA of cholesterol 7α-hydroxylase and a host cell comprising the vector. Further, an expression vector can comprise a construct of a cholesterol 7α-hydroxylase promoter region operably linked to a reporter gene. Such a construct can be introduced into a mammal at an embryonic stage to provide a transgenic nonhuman mammal. Thereby, advantageously, germ cells and somatic cells of the mammal contain a promoter region from the human genomic CYP7 5' flanking sequence of the human cholesterol 7α-hydroxylase gene, wherein the promoter region is operably linked to a reporter gene.

The transgenic mammal described above containing the reporter construct can be used to screen or determine an agent's capacity to up- or down- regulate the promoter region of human cholesterol 7α-hydroxylase. This is achieved by exposing the mammal to a test agent and detecting an effect the expression of reporter gene in the mammal relative to that of a control, where no agent is applied. For example, when the mammal is exposed to agents that upregulate the promoter region of human cholesterol 7α-hydroxylase, expression of reporter gene is increased, and the agent is identified as potentially capable of decreasing serum cholesterol in humans.

Another embodiment of the invention provides a transformed cell comprising a recombinant human cholesterol 7α-hydroxylase gene which is operably linked to a cis-acting regulatory element that controls expression of said gene and wherein the recombinant human cholesterol 7α-hydroxylase gene sequence is substantially the same as the coding sequence of human cholesterol 7α-hydroxylase gene.

Another embodiment provides a cell, wherein transcription of recombinant human cholesterol 7α-hydroxylase gene is under the control of cis-acting regulatory elements/promoter that are the same as the sequences controlling the transcription of the endogenous human cholesterol 7α-hydroxylase gene, and wherein a cis-acting regulatory element controlling transcription of said gene is inducible.

Another object of the invention is to provide a cholesterol 7α-hydroxylase minigene for transforming an animal to produce functionally active cholesterol 7α-hydroxylase. A minigene of CYP7 in this context can comprise exons I through VI inclusive and at least two introns selected from the group consisting of I and II; and I, II and III. Optionally, the minigene can further comprise a CYP7 promoter region.

Another transgenic nonhuman mammal is provided according to the invention, the mammal having germ cells and somatic cells that comprise a recombinant human cholesterol 7α-hydroxylase gene that is operably linked to a cis-acting regulatory element that controls the expression of the gene in said mammal such that peripheral blood cholesterol levels and the production of bile acids in said mammal are affected. The gene is introduced into the non-human mammal or an ancestor of the non-human mammal at an embryonic stage, and a chromosome of said mammal includes an endogenous coding sequence substantially the same as the coding sequence of the human cholesterol 7α-hydroxylase gene. Such a transgenic mammal is provided, wherein transcription of recombinant human cholesterol 7α-hydroxylase gene is under the control of those cis-acting regulatory elements/promoter sequences that control transcription of the endogenous human cholesterol 7α-hydroxylase gene, and wherein the cis-acting regulatory element controlling transcription of said gene is inducible.

BRIEF DESCRIPTION OF THE DRAWINGS

FIG. 3 shows a human CYP7 amino acid sequence (SEQ ID NO:3) that is expressed in a transgenic animal carrying a minigene.

FIG. 4 shows a nucleotide sequence (SEQ ID NO:4) including exon I, intron I, exon II, intron II and exon III, of human CYP7.

FIG. 5 shows a nucleotide sequence (SEQ ID NO:5), including 5' upstream Eco RI fragment.

FIG. 6 shows a nucleotide sequence (SEQ ID NO:6), including intron IV exon V, intron V, and exon VI, of human CYP7.

DETAILED DESCRIPTION OF PREFERRED EMBODIMENTS

Figure 1:
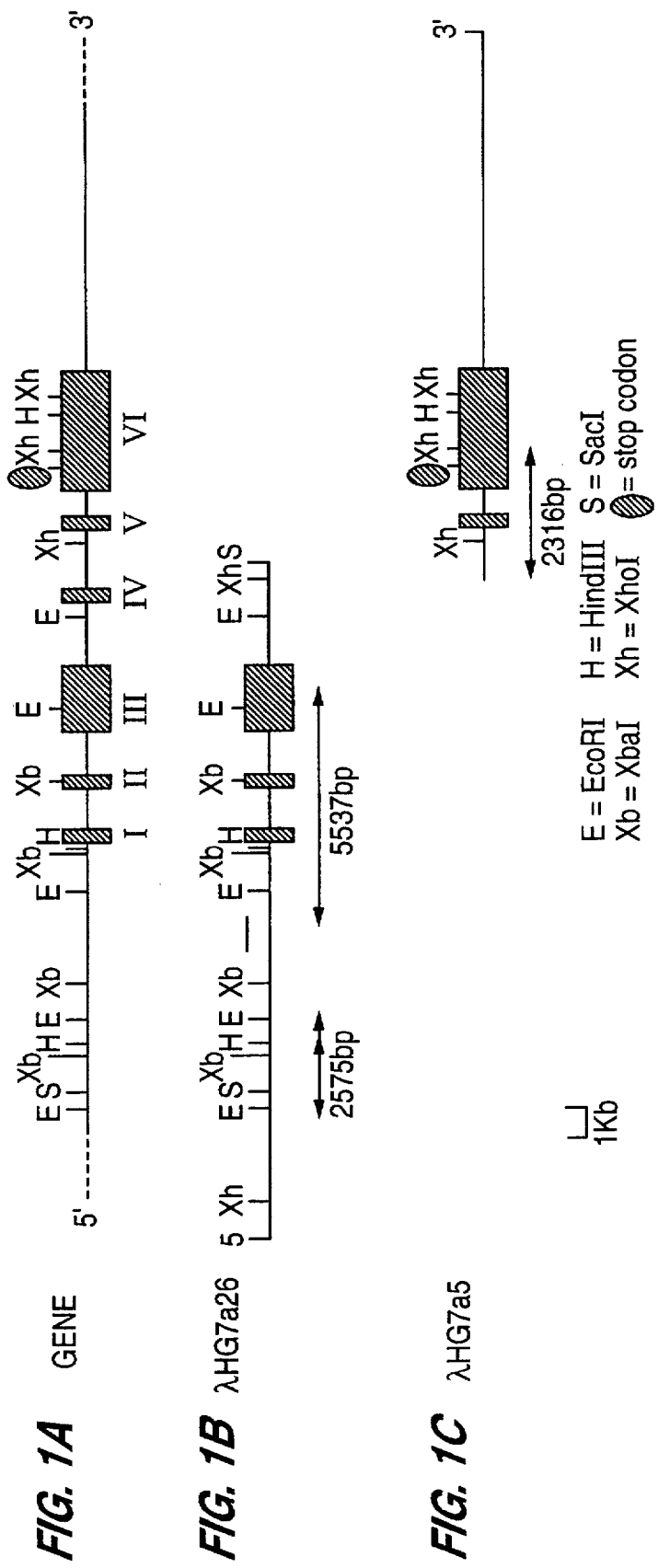
FIG. 1A shows a gene map of the human CYP7 gene.
FIG. 1B and FIG. 1C show the gene map of clones λHG7α26 and λHG7α5, respectively. Exons I, II and III are represented by shaded boxes. Arrows indicate regions where sequences have been determined (shown in FIGS. 4, 5 and 6 (SEQ. ID NOS 4, 5 and 6, respectively)).

The present invention relates to the isolation and sequencing of the human genomic CYP7 gene, including intron and exon sequences and 5' upstream sequences. Two clones containing genomic CYP7 DNA are sequenced, as shown schematically in FIGS. 1B and 1C. The invention also includes a recombinant vector containing at least a fragment of the genomic CYP7 gene and a host cell, such as E. Coli, containing the vector.

The invention further includes "fragments" of the CYP7 genomic DNA, exemplified by a DNA fragment that is an exon or intron of the CYP7 gene. In FIG. 4 (SEQ ID NO:4), exon I is nucleotides 2236 to 2319, intron I is 2320 to 3928, exon II is 3929 to 4169, intron II is 4170 to 5210, and exon III is 5211 to 5537. In FIG. 6 (SEQ ID NO:6), partial exon IV is 1 to 456, exon V is 457 to 632, intron V is 633 to 1220, and exon VI begins at 1221 of FIG. 6. The category of "fragment" within the present invention also encompasses any fragment obtained by digesting the disclosed DNA of the invention with any restriction endonucleases, preferably, at the restriction sites shown in FIG. 1. Other restriction fragments can be obtained as well, by using conventional skills in the art.

Also encompassed by the present invention are DNA sequences that hybridize under stringent conditions, preferably high stringent conditions, with any of the DNA sequences or fragments mentioned above. According to the present invention the term "stringent conditions" means conditions with a salt concentration of 4× SSC (NaCl-citrate buffer) at 62°–66° C., and "high stringent conditions" means conditions with a salt concentration of 0.1× SSC at 68° C.

From the determined gene sequence of human CYP7, a promoter region of the gene is further identified. Clone λHG7α26 contains an insert that spans about 8.0 kb of the 5'-upstream flanking sequence. According to the invention, this sequence information permits construction of a human CYP7 promoter operably linked to a reporter gene. This "promoter/reporter" gene construct is used to transform host cells and animals. For example, the promoter/reporter gene is used to transform E. coli strain JM101 or mammalian hepatocytes, or to transform a transgenic mouse or hamster.

In another embodiment of the invention, a transformed cell line or transgenic animal containing a promoter/reporter gene according to the invention is provided. Such a transformant readily detects an agent that increases or decreases expression of CYP7 gene. This is so because the agent's interaction with the CYP7 promoter region produces a corresponding reporter protein expression pattern that is easily detectable. For example, where the firefly-derived protein luciferase is used as a reporter gene, luciferase expression is measured quantitatively by its bioluminescence.

The CYP7 promoter region or certain regulatory elements excised therefrom can be used for the controlled expression of either the CYP7 gene or various reporter or indicator genes which allow quantitative determination of gene expression in the presence of inhibitory or stimulatory drugs. Reporter genes include, but are not limited to, E. coli β-galactosidase, galactokinase, interleukin 2, thymidine kinase, alkaline phosphatase, luciferase and chloramphenicol acetyltransferase (CAT). Such an expression system can, therefore, also be used for screening compounds for their ability to inhibit or stimulate expression of a structural gene.

In another embodiment, a minigene construct is provided by ligating a fragment of newly discovered genetic information, in particular a gene sequence excised from clone λHG7α26, together with a cDNA spanning exons 3–6. According to the present invention, a minigene is provided and used to transform an animal for in vivo production of human CYP7.

Figure 2:
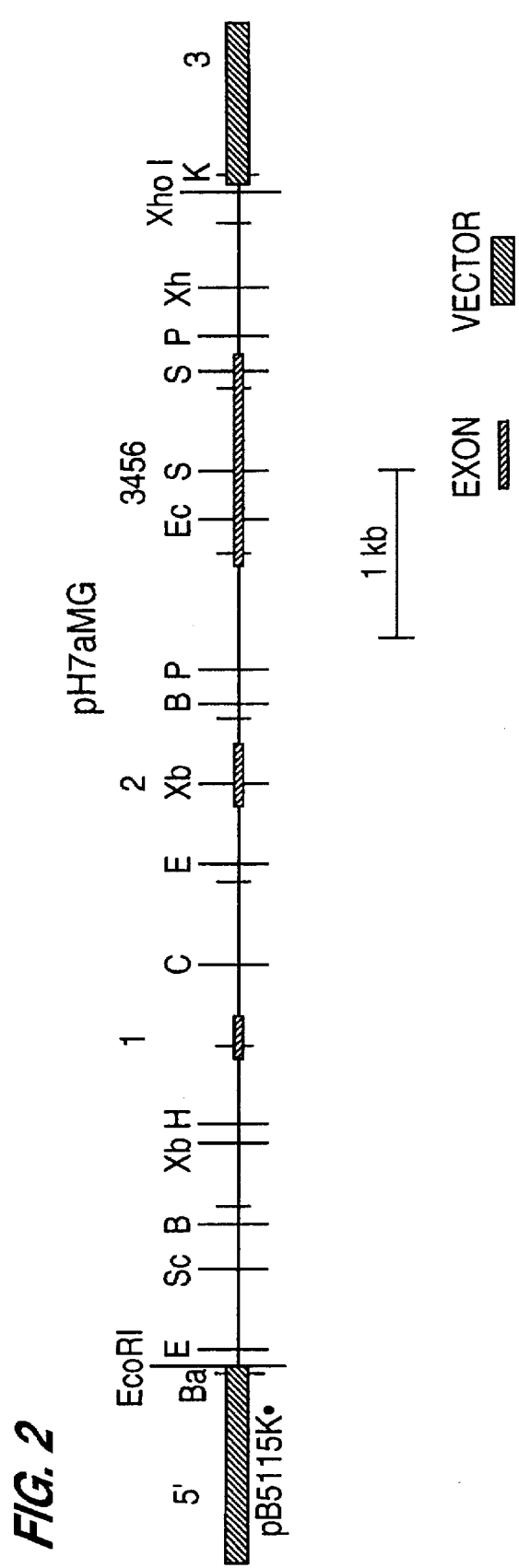
FIG. 2 is a diagrammatic representation of the construction of the human cholesterol 7α-hydroxylase containing plasmid, pH7 aMG. Shaded thin boxes represent amino acid coding exons, while vector is represented by shaded thick boxes. A 5.5 kilobase EcoRI fragment (FIG. 4 SEQ ID NO:4) which contains promoter region, exons I, II and partial exon III and introns I and II, was fused to a EcoRI-XhoI fragment of cDNA which contains partial exon III, exons IV, V and partial exon VI. An internal EcoRI site in exon III provided the linkage of the gene fragment to the cDNA to construct a minigene, as discussed in Example III. Restriction enzyme cleavage sites are as follows: Ba=BamH1, Ec=EcoR1, E=EcoR V, Sc=Sca 1, B=Bgl 11, Xb=Xba1, H=HinD111, C=Cla 1, P=Pst 1, Xh=Xho 1, S=Sma 1, K=Kpn 1.

In making a minigene in accordance with the invention, a promoter region and exons I-VI are employed, as well as introns I and II, or introns I, II and III of the genomic CYP7 DNA. However, any of introns III, IV or V may be omitted. For example, introns III, IV and V or introns IV and V of the CYP7 gene can be omitted. Thus a preferred minigene according to the invention contains all of the CYP7 exons as well as introns I and II. Another minigene according to the invention contains all exons and introns I, II and III. Therefore, a method is provided for expressing a CYP7 gene in transgenic animals that have been transformed with a minigene, such as the minigene shown in FIG. 2.

Optionally the minigene can contain the promoter region of CYP7. Alternatively, another known promoter region is substituted for the promoter region of CYP7 to permit experimentally regulated promoter-driven expression in an animal. For example, a transgenic mouse can be made wherein the CYP7 minigene is driven by the metallothionein promoter. Use of this promoter in a transgenic mouse provides a model of CYP7 overexpression in the transgenic animal.

In another embodiment of the invention, a human CYP7 minigene permits production of a transgenic animal, preferably an animal that carries new genetic information in every tissue, including the germ cells. A minigene, when introduced into a transgenic animal, will express a CYP7 protein having an amino acid sequence (SEQ ID NO:3) shown in FIG. 3. This animal is a useful disease model for screening an agent in vivo effect on the regulation of CYP7 expression, as described further in Example 3.

Various methods are employed to introduce foreign genes into animals. These methods include: micro-injection of DNA into single cell embryos, retroviral infection of embryos and calcium phosphate-mediated DNA uptake by embryonic stem cells. Hogan et al., MANIPULATING THE MOUSE EMBRYO; A LABORATORY MANUAL (Cold Spring Harbor Laboratory, 1986); Leder et al., U.S. Pat. No. 4,736, 866; Leder et al., U.S. Pat. No. 5,175, 383; Krimpenfort et al., U.S. Pat. No. 5,175,384, the contents of each of which are hereby incorporated by reference.

The most successful and most preferred technique is microinjection of DNA. Hammer et al., J. Anim. Sci. 63: 269 (1986); Gordon et al., Science 214: 1244 (1981); Brinster et al., Proc. Natl. Acad. Sci. USA 82: 4438 (1985). Microinjection involves the isolation of embryos at the single cell stage. The DNA encoding the gene of interest is microinjected in vitro into the isolated embryos and the manipulated embryos are implanted into pseudo-pregnant females. Transgenic animals can be identified shortly after birth by analyzing the DNA obtained from a tissue fragment, such as the tail, using probes specific for the inserted gene. Integration has been generally found to occur in a head-to-tail concatameric fashion at a single genomic site. Incorporation of the foreign gene at the one-celled stage results in a transgenic animal; if integration occurs at a multicellular stage, a mosaic results. Integration of two different embryonic stem cells may lead to the creation of a chimeric animal. Only microinjection results in the production of animals that can transmit the genetic information to their progeny in a Mendelian fashion. Germline integration is essential in order to utilize these transgenic animals as perpetual animal models.

Introduction of the recombinant human cholesterol 7α-hydroxylase gene at the fertilized oocyte stage ensures that the gene sequence will be present in all of the germ cells and somatic cells of the transgenic "founder" animal. The presence of the recombinant gene sequence in the germ cells of the transgenic founder animal means that approximately half of the founder animal's descendants will carry the activated recombinant gene sequence in all of their germ cells and somatic cells.

Several factors determine the level at which the new protein will be expressed, as well as its temporal and tissue-specific manner of expression. Perhaps the most important factors are the promoter and enhancer employed in controlling the expression of the protein encoded by the inserted DNA. Regulatory elements which are tissue-specific direct significant expression to a specific tissue; whereas ubiquitous promoters permit expression in different tissues within the animal.

Important cis-acting regulatory elements, other than the 5' upstream region, are required for expression of a human gene at levels equivalent to or higher than that in the unmodified organ. It is known that the first intron and second intron and possibly third intron of a human gene are important in the regulation of protein expression.

Furthermore, the presence of intronic sequences within the transgene have been shown to eliminate or at least dampen inhibitory effects of the site of DNA integration into the genome. Behringer et al., Science 245:971 (1989); Lang et al., EMBO J. 7:1675 (1988). For example, in order to overcome the positional effects of integration upon expression levels, the prior art has positioned enhancer regions 10–50 kb upstream, introns, or parts of introns close to splice junctions in the DNA constructs for transgenic animal production. Brinster et al., Proc. Natl. Acad. Sci. USA 85:836 (1988); Buchman et al., Mol. Cell Biol. 8:4395 (1988). Therefore, one of ordinary skill in this art, given the DNA sequence of the present invention, would be able to construct various combinations of cis-acting regulatory elements of the human cholesterol 7α-hydroxylase gene to test which regions are required for expression of the human gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

In general, the invention features a transgenic non-human vertebrate animal, preferably a mammal such as a rodent, eg., a mouse or hamster, containing germ cells and somatic cells that contain a recombinant gene which is substantially homologous with a vertebrate gene in the cholesterol 7α-hydroxylase family which is capable of expressing cholesterol 7α-hydroxylase. The recombinant gene is introduced into the animal, or an ancestor of the animal, at an embryonic stage, preferably the one-cell, or fertilized oocyte stage, and generally not later than about the 8-cell stage. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans. The term endogenous cis-acting regulatory elements refers to the nucleic acid sequence that controls the expression of the human cholesterol 7α-hydroxylase gene in vivo.

The animals of the invention can be used as models to test for agents that potentially effect the expression of human cholesterol 7α-hydroxylase. The use of transgenic animals to test for agents that effect: (1) the expression of various enzymes involved in cholesterol metabolism and (2) atherosclerosis is well known to those of skill in the art, as described by Breslow, *Proc. Natl. Acad. Sci. USA* 90:8314 (1993), the entire contents of which are hereby incorporated by reference. Since human cholesterol 7α-hydroxylase is the rate limiting enzyme controlling peripheral blood cholesterol levels, the consequent occurrence of hypercholesterolemia in humans is dependent upon the levels at which this enzyme is expressed. Hypercholesterolemia (or hypercholesteremia or hypercholesterinemia) is a clinical condition in which there is an abnormally large amount of cholesterol present in the cells and plasma of the circulating blood. Hypercholesterolemia is a serious medical condition that leads to atherosclerosis, atheromatous plaques, arteriole sclerotic plaque formation, hypertension and heart disease. The transgenic animals of the invention can be used for testing agents that may cure hypercholesterolemia, or relieve its symptoms, or for testing agents that may promote hypercholesterolemia.

The agents to be tested can be administered to an animal of the invention and the animal's peripheral cholesterol and bile acids are monitored. Peripheral cholesterol is measured by routine tests available in most clinical laboratories. Bile acid production is monitored using reverse phase high pressure liquid chromatography (HPLC).

Transgenic animals of the invention are most useful as animal models for testing agents and procedures that promote or inhibit overexpression or under expression of CYP7. Overexpression would result in increased bile acid synthesis from cholesterol whereas underexpression would result in decreased bile acid synthesis from cholesterol and hypercholesterolemia. Therefore, transgenic animals of the invention may be used to study the regulation of bile acid synthesis and hypercholesterolemia. In particular, a transgenic mouse or hamster on a high cholesterol diet is used to determine whether overexpression of CYP7 in the mice could prevent hypercholesterolemia. Transgenic mice fed a diet containing high levels of both bile acids and cholesterol are used to determine whether a high bile acid diet suppresses 7α-hydroxylase expression and thus induces hypercholesterolemia.

The constructs of the present invention may be used to assess gene expression in vitro as well as gene regulation in vivo. For example, the construct of FIG. 2 may be used to transfect hepatocytes and other mammalian cells to test for tissue specific expression of the CPY7 gene. Also, the construct of FIG. 7 may be used to transfect hepatocytes and other mammalian cells to assess the regulation of the CPY7 gene.

In general, the invention features a transformed mammalian cell, preferably a hepatocyte, containing a recombinant gene which is substantially homologous with a vertebrate gene in the cholesterol 7α-hydroxylase family which is capable of expressing cholesterol 7α-hydroxylase. The recombinant gene is introduced into the cell by various transfection means well known in the art. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans.

The cells of the invention can be used as models to test for agents that potentially affect the expression of human cholesterol 7α-hydroxylase. The agents to be tested can be provided to the cells and the expression of human cholesterol 7α-hydroxylase assayed. Such transformed cells are useful for testing agents that promote or inhibit overexpression or under expression of CYP7.

Analysis of the CYP7 promoter may be performed in cell culture using either the downstream recombinant CYP7 minigene or a reporter construct. The CYP7 regulatory elements can be used for the controlled expression of either the CYP7 gene or various reporter or indicator genes which allow quantitative determination of gene expression in the presence of inhibitory or stimulatory drugs. Reporter genes and systems have been described herein.

The following examples illustrate the invention and, as such, are not to be considered as limiting the invention set forth in the claims.

EXAMPLE 1

GENOMIC DNA OF CYP7 HUMAN CHOLESTEROL 7α-HYDROXYLASE

A human genomic library constructed with Sau3A1 partially digested human placental DNA ligated into a BamHI site of EMBL-3 Sp6/T7 phage vector (Clontech, Palo Alto, Calif.) was screened using a 1.6 kb EcoRI-PstI fragment of a human cholesterol 7α-hydroxylase cDNA isolated previously (Keram and Chiang, Biochem. Biophys. Res. Comm. 185, 588–595, 1992) as a hybridization probe. Hybridizations were carried out at a high stringent condition of 68° C., 1% SDS and 0.1× SSC. 800,000 pfu of phages were screened. After four cycles of screening, seven positive clones were plaque-purified. Three clones containing the largest inserts (λHG7α26, λHG7α5 and λHG7α52) were isolated and analyzed by restriction mapping. FIG. 1B shows the gene map of clone λHG7α26, which contains a 15 kb insert that spans about 8.0 kb of the 5'-upstream flanking sequence and exons I to III FIGS. 4 and 5 SEQ ID NOS 4, 5 and 6, respectively). Clone λHG7α5 (FIG. 1C) contains intron IV, exon V, intron V and partial exon VI (FIG. 6 SEQ ID NO:6). An 8.0 kb 3'-flanking sequence extends beyond the sequenced region of λHG7α5 (FIG. 6 SEQ ID NO:6).

Bacteriophage clones λHG7α26 and λHG7α5 both were deposited August 25, 1993 at the American Type Culture Collection, ATCC, 12301 Parklawn Drive, Rockville, Md. 20852, USA under the accession numbers ATCC 75534 and ATCC 75535, respectively.

Five EcoRI fragments of the clone λHG26 were excised from the phage DNA insert by restriction digestion and shotgun subcloned into phagemid vector pBluescript II KS+ (Stratagene, La Jolla, Calif.). The clones were size-selected and EcoRI fragments were isolated from CsCl purified plasmids and used for sequencing: Nested deletions were generated by ExoIII/Mung Bean nuclease digestion according to manufacturer's instruction (Stratagene, Calif.) using the conditions of 37° C. incubation for 1 min intervals. This condition resulted in an average deletion of about 200 to 250 bp/min. DNA sequencing of the nested deletions were carried out by the dideoxy chain termination method using T7 sequenase version 2.0 (USB, Cleveland, Ohio) and $^{35}$S-dATP. Sequence data were obtained from both strands and the overlapping deletion clones and analyzed using DNASIS software (Hitachi America, Calif.). Nucleotide sequences of a 5 kb EcoRI fragment and a 2.6 kb EcoRI fragments were determined. The 5 kb fragment contains the sequence from −1886 of the 5'-upstream region to partial exon 3 (FIG. 4 SEQ ID NO:4). Included in FIG. 4 is a 347 bp 3'-end sequence of a 3.5 Kb EcoRI fragment located immediately upstream of this 5 Kb fragment and a 233 bp 5' end sequence of a 2.6 kb EcoRI fragment immediately downstream of a 5 kb fragment. As shown in FIG. 1B, the 2.6 kb fragment (FIG. 5 SEQ ID NO:5) is located further 5' of the 3.5 kb EcoRI fragment. Thus, about 4875 bp of the 5'-upstream flanking region sequence of the gene were determined.

A comparison of sequences of the present invention to those of Molowa et al. (1992) in the overlapping region (1604 bp) revealed that sequences from the transcription start site to about −460 are identical; however, further upstream sequences vary significantly. A total of 52 sequence discrepancies were found, not all of are attributed to the presence of polymorphisms in the human genes. Cohen at al. (Genomics, 14, 153–161, 1992) reported a 723 bp upstream sequence. Seven mismatches in Cohen's sequence from +1 to −723 were identified. A "T" to "C" conversion at nucleotide −469 was identified to be a Mae II polymorphism (Thompson et al., Biochem. Biophys. Acta. 1168, 239–242, 1993). The 5'-flanking sequence of the present invention was identical to that reported by Thompson et al., (1993), with the exception of a mismatch at nucleotide −1197, found in the overlapping region from +1 to nucleotide −2235. No intron sequences have been reported by other laboratories.

Clone λHG7α5 was also sequenced from the 5' end of the gene. FIG. 6 (SEQ ID NO:6) is the 2316 basepair sequence that contains partial intron IV, exon V, intron V and exon VI of the human CYP7 gene.

EXAMPLE 2

PROMOTER/REPORTER TRANSGENIC ANIMAL

Figure 7:
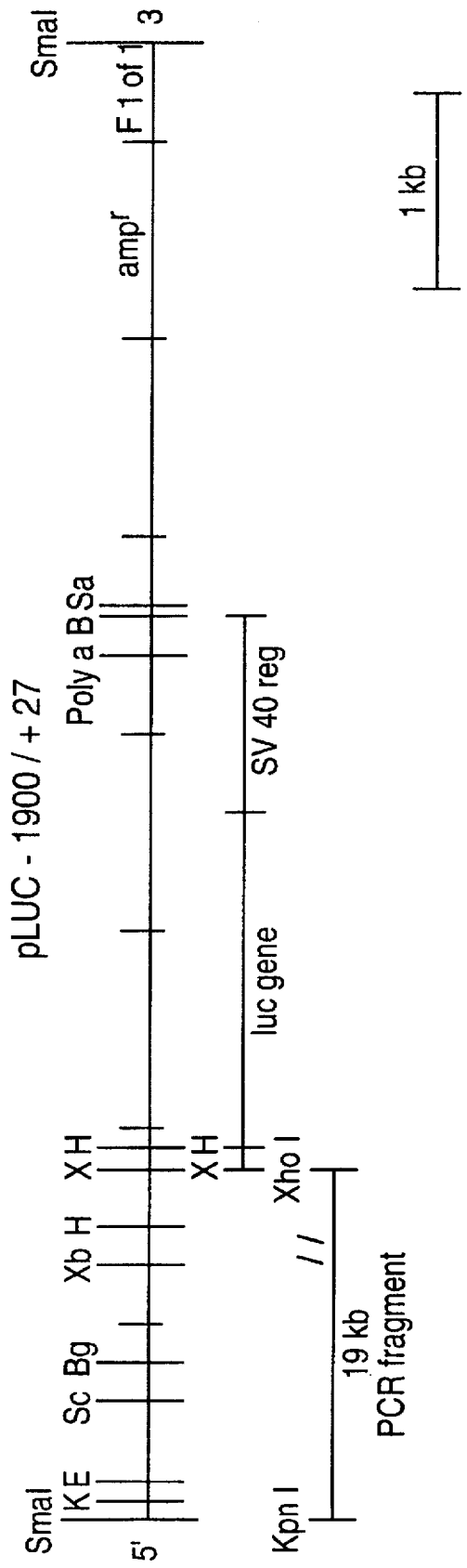
FIG. 7 is a diagramatic representation of the construction of the luciferase reporter gene vector that includes the 5' sequence from the human genomic cholesterol 7α-hydroxylase gene, and the reporter luciferase gene described in Example 2. Restriction enzyme cleavage sites are as follows: K=Kpn 1, E=EcoR1, Sc=Sca 1, Bg=Bgl 11, Xb=Xba 1, H=Hind 111, X=Xho 1, B=BamH 1, Sa=Sal 1.

Assessment of gene regulation in transgenic animals using the luciferase reporter system is well known to those of skill in the art. DiLelia et al., Nucl. Acids. Res. 16:4159 (1988), incorporated by reference in its entirety. Vectors for producing such reporter constructs are commercially available from Promega Corporation (2800 Woods Hollow Road, Madison Wis. 53711-5399). For example, the pGL2-Basic luciferase vector (Promega) may be used to construct a cassette that will report the important cis-acting elements in the CYP7 5' sequence from the human genomic cholesterol 7α-hydroxylase gene. As shown in FIG. 7, a 1.9 kb promoter region of the human genomic clone HG7a26 from −1879 to +24, which is equivalent to nucleotides 2236 through 4139 of FIG. 4 (SEQ ID NO:4), was obtained by PCR amplification. A Kpn 1 site was introduced at the 5' end using an HLU-1 primer (HLU-1 primer= 5'TACCGCTCGAGTGATTAGAAAGGGAAGGAT3' SEQ ID NO:1) and an Xho 1 site was introduced at the 3' end using an HLU-2 primer (HLU-2 primer= 5'=CAAGAATGATAGATAAAAT 3'SEQ ID NO:2). This recombinant Kpn 1-Xho 1 fragment containing the human cholesterol 7α-hydroxylase promoter region was ligated into the luciferase vector pGL2-Basic (Promega), which had been cut with restriction enzymes Kpn 1 and Xho. The resulting promoter-luciferase reporter chimeric construct was purified and used to transform host cells, such as the E. coli strain JM101.

The entire 1.9 kb human cholesterol 7α-hydroxylase promoter region and luciferase reporter gene, including a poly(A) signal, is flanked by unique Kpn 1 and BamH 1 restriction enzymes sites. The Kpn 1 and BamH1 fragment is 4.6 kb and is used for microinjection into fertilized oocytes in the production of transgenic animals. Transgenic animals containing this construct, as assayed by Southern Blot analysis, are then tested for various agents which are capable of upregulating or downregulating the CYP7 cis acting elements. Alternatively, given the DNA sequence of the present invention, one of skill in the art is able to contruct various combinations of cis-acting regulatory elements of the human cholesterol 7α-hydroxylase gene to test the specific regions and positional affects that are required for expression of the human cholesterol 7α-hydroxylase gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

Tissue samples, including liver, are tested for luciferase activity by methods well known in the art. Promega Notes 28:1 (1990); Promega Technical Bulletin (Promega Corporation, September 1993); Wood, BIOILLUMINESCENCE AND CHEMILUMINESCENCE (John Wiley and Sons, 1991). Briefly, the homogenized tissue supernatants are mixed with luciferin and Coenzyme A in a buffer containing ATP. Luciferin illuminescence, as detected using a luminometer, only occurs in the presence of the recombinant luciferase expressed in the transgenic tissue.

EXAMPLE 3

PRODUCTION & ANALYSIS OF TRANSGENIC MICE CONTAINING DNA ENCODING HUMAN GENOMIC CHOLESTEROL 7A-HYDROXYLASE

The recombinant CYP7 minigene present in the pH7 aMG vector is incorporated into the germ cells of mice as follows: The construction of the pH7aMG shown diagrammatically in FIG. 2. The entire 7.2 kb insert in pH7aMG can be removed by restriction enzyme cleavage with BamH 1 and Kpn 1. The CYP7 minigene DNA was prepared for injection by digestion with 4 units each of BamH1 and Kpnl per ug of DNA per 1 hour at 37° C, electrophoresed through a 1% agarose gel, and purified as described by Sinn et al., *Cell* 49: 465 (1987). The isolated 7.2 kb DNA fragment was injected into the pronuclei of fertilized one-cell mouse or hamster eggs derived from the FVB/NHd inbred strain (Taconic laboratory, Germantown, N.J.). About 100 to 1000 copies of linearized plasmid is incorporated per pronucleus. Following microinjection, viable eggs are transferred to the oviducts of pseudopregnant Swiss Webster mice (Taconic Farms), as described by Wagner et al., *Proc. Natl. Acad. Sci. USA* 78:5016 91981). Mice are housed in an environmentally controlled facility maintained on a 10 hour dark: 14 hour light cycle. The eggs in the foster females are allowed to develop to term.

Between two and six weeks of age, the DNA of each pup born is analyzed by Southern hybridization using DNA taken from the pup's tail. DNA is extracted from 1.5 cm tail sections. Davis et al. *Meth. Enzym.* 65:405 (1980). The nucleic acid pellet is resuspended in 200 μl of 10 mM Tris-Cl pH 7.4, 0.1 mM EDTA, and 10 μg is digested with Kpn1 and BamH1, electrophoresed through 1.0% agarose, and transferred to nitrocellulose. Southern, *J. Mol. Biol.* 98:503 (1975). Filters are hybridized overnight to CYP7 transgene specific probe in the presence of 10% dextran sulfate and washed twice in 2× SSC, 0.1% SDS at 64° C. A CYP7 transgene specific probe is a fragment of the CYP7 minigene that will not hybridize to related sequences in the host genome. This fragment is free of repetitive sequences. The CYP7 transgene specific probe is labeled with $^{32}$P dCTP by nick translation. Rigby et al., *J. Mol. Biol.* 113:237 (1977).

Southern hybridization indicates which founder mice retain the CYP7 minigene construct.

3.1 Transcription of the Human Cholesterol 7α-hydroxylase Minigene in Transgenic Mice Transcription of the newly acquired gene in tissues was determined by extracting RNA from the tissues and assaying the RNA by Northern Blot analysis. The excised tissue is rinsed in 5.0 ml cold Hank's buffered saline and total RNA is isolated by methods employing a CsCl gradient. Chirgwin et al. *Biochem.* 18:5294 (1979). RNA pellets are washed twice by reprecipitation in ethanol and quantitated by absorbance at 260 nm. Single stranded, uniformly labeled RNA probe is prepared using a transgene specific probe. Such a transgene specific probe is a fragment of the CYP7 minigene that will not hybridize to related sequences in the host genome. This fragment is free of repetitive sequences. Since the human cholesterol 7α-hydroxylase mRNA is 3 kb and the endogenous mouse cholesterol 7α-hydroxylase mRNA is 4 kb, even the entire CYP7 minigene construct cut out of the pH71 MG could be used to identify the presence of the transcribed exogenous human cholesterol 7α-hydroxylase gene. Melton et al., *Nucl. Acids Res.* 12:7035 (1984).

To test for transcription of the CYP7 minigene, labelled single-stranded probe fragments are isolated on 8M urea 5% acrylamide gels, electroeluted and hybridized to total RNA. Berk et al., *Cell* 12:721 (1977). The hybridization mixture contains 50,000 CPM to 100,000 cpm of probe (Specific Activity ~$10^8$ cpm/μg), 10 μg total cellular RNA, 50% formamide, 500 mM NaCl, 20 mM Tris pH 7.5, 1 mM EDTA. Melton et al. (1984) supra. Hybridization temperatures vary according to the GC content. The hybridizations are terminated by the addition of 1500 units of RNAase A and RNAase T$_1$ (Sigma, St. Louis, Mo.). RNAase digestions are carried out at 37° C. for 15 minutes. The samples are then ethanol precipitated and electrophoresed on 8M urea 5% acrylamide gels.

The tissues analyzed are liver, muscle, pancreas, stomach, brain, intestines, eye, aorta, salivary gland and kidney. 10 μg of total RNA from each of these tissues is analyzed using a transgene specific probe.

In situ hybridization, using the transgene specific probe, of the histologic sites that transcribe the CYP7 minigene confirm the presence of the exogenous cholesterol 7α-hydroxylase gene in the transcribing tissues.

3.2 Localization of Transgene Expression mRNA transcripts are evaluated in liver RNA (prepared as above) after conversion to cDNA, PCR amplification and Southern hybridization analysis. Rosenfeld et al., supra. To ensure that CYP7 transgene is specifically evaluated and that the 5' and 3' portion of mRNA transcripts are present, two separate primer pairs are used: a 5' primer pair to detect the 5' end of recombinant construct mRNA transcripts and a CYP7-specific antisense primer, and a 3' primer pair to evaluate the 3' end of the recombinant mRNA transcript. Fiers et al., *Nature* 273:113 (1978)

PCR amplification products are evaluated by agarose gel electrophoresis followed by Southern hybridization using $^{32}$P-labeled human CYP7 probes.

Northern analysis of liver RNA from transgenic animals will exhibit CYP7 directed human mRNA transcripts of a size similar to that directed by these constructs in cultured cells. Levels of a constitutively expressed protein transcripts, such as Beta-actin or glyceraldehyde-3-phosphate dehydrogenase, serve as a positive control and are normally similar for both transgenic and nontransgenic tissue samples.

3.3 Expression of Recombinant Human Cholesterol 7α-hydroxylase in Transgenic Animal Tissues Expression of the human cholesterol 7α-hydroxylase transgene is evaluated by Western Blotting or immunohistochemistry. Alternatively, expression of a linked reporter gene, such as luciferase or LAC-Z, may be used to quantitate the tissues or cells expressing the transgene. For western blot or immunohistochemical detection of transgenically expressed protein, antibodies specific for human cholesterol 7α-hydroxylase are used to detect the presence of this enzyme in various tissue sections or protein preparations from various tissues. Antibodies specific for human cholesterol 7α-hydroxylase are described in J. Chiang (Attorney docket 18748/176, U.S. Ser. No. 08/135,510 U.S. Pat. No. 5,420,028). Briefly, 1 mg purified CYP7 enzyme is mixed with an equal volume of Freund's adjuvant and 5 mg/ml of heat-killed microbacteria. The emulsified antigen mixtures were injected on the back of New Zealand white rabbits by intradermal injections on multiple sites. After six weeks, 0.5 mg of purified human enzyme was mixed with incomplete adjuvant and used for booster injections to the same rabbits. Six weeks later, blood samples were collected from ear veins and tested for the presence of antibodies by Ouchterlony double diffusion and by immunoblotting as described previously by Chiang, et al., *J. Biol. Chem.* 265, 3889–3897 (1990), incorporated by reference in its entirety. For immunoblot analysis, one μg of purified human CYP7 enzyme was loaded on a 7.5% SDS-polyacrylamide gel, separated polypeptides were electrophoretically transferred to an Immobilon P membrane by a modified procedure reported previously (Chiang et al., supra. (1990)). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

The presence of human 7 alpha-hydroxylase expression in tissues is evaluated by immunohistochemistry using a human 7 alpha-hydroxylase specific antibody. The alkaline phosphatase monoclonal anti-alkaline phosphatase method is used to detect binding of the specific antibody to various tissue sections.

EXAMPLE 4

ANIMAL TESTING

Transgenic animals of the invention are most useful as animal models for testing agents and procedures that promote or inhibit overexpression or under expression of CYP7. The CYP7 expressing animals are tested for materials that are suspected of promoting or inhibiting hypercholesterolemia. The animals are exposed to various dosages of a known agent and tested for peripheral blood cholesterol and bile acid production. Animals and their descendants that have either increased or decreased peripheral blood cholesterol levels are then tested for the effect of an agent on the expression of CYP7.

Transgenic animals treated with agents that cause overexpression of CYP7 are used to study whether such overexpression prevents hypercholesterolemia when such treated animals are on a high cholesterol diet. Also, transgenic mice fed a diet containing high levels of both bile acids and cholesterol are used to determine whether a high bile acid diet suppresses 7α-hydroxylase and thus induces hypercholesterolemia.

EXAMPLE 5

TISSUE CULTURE OF TRANSGENIC CELL LINES

The transgenic animals of the invention can be used as a source of cells for cell culture. Cells of the tissues of the transgenic animal that contain the activated recombinant gene can be cultures, using standard tissue culture techniques and used, for example to study the causes of hypercholesterolemia at the cellular and tissue level.

EXAMPLE 6

PRODUCTION OF TRANSFORMED CELLS: PROMOTER/REPORTER GENE CONSTRUCTS

Assessment of gene regulation in transformed mammalian cells using the luciferase reporter system is well known to those of skill in the art. deWet et al., *Mol. Cell. Biol.* 7: 725 (1987). The same pGL2-Basic luciferase vector (Promega) constructs described for the transgenic animals may be used in vitro. Also, luciferase activity in cell culture is performed by methods well known in the art. *Promega Notes* 28:1 (1990); *Promega Technical Bulletin* (Promega Corporation, Sep. 1993). Briefly, the supernatants of lysed cells are mixed with luciferin and Coenzyme A in a buffer containing ATP. Luciferin illuminescence, as detected using a luminometer, only occurs in the presence of the recombinant luciferase expressed in the transformed cells.

The transformed promoter-reporter cells of the invention can be Used as models to test for agents that potentially effect the expression of human cholesterol 7α-hydroxylase.

To determine the promoter sequences responsible for regulation of cholesterol 7α-hydroxylase, deletions of the human CYP7 cis-acting elements are ligated upstream of the luciferase reporter gene (Luc). The promoter fragments were generated by the polymerase chain reaction using the primers and a human CYP7 genomic clone as the template. The fragments were blunted by filling in with the Klenow fragment of DNA polymerase and then digested with Xho I. The fragments were then ligated into pGL2-basic vector (Promega) which had been digested with SmaI and Xho I, and transformed into *E. coli* HB101 cells. The resulting plasmids could be used to transfect primary hepatocytes or hepatoma cells for the study of human luciferase gene expression under the control of the human CYP7 promoter.

Chloramphenicol acetyltransferase (CAT) reporter gene constructs were made by using the polymerase chain reaction and primers to amplify the 5' flanking regions and introns 1, 2 and 3 of the human CYP7 gene. Fragments are ligated into a promoterless pCAT basic vector (Promega). This plasmid is then used to generate nested deletions containing various pieces of 5' flanking DNA, intron 1, intron 2 and/or intron 3.

EXAMPLE 7

PRODUCTION OF TRANSFORMED CELLS: MINIGENE CONSTRUCTS

The DNA of each transformed cell line from each construct is analyzed by Southern hybridization. DNA is extracted from the cells culture and the nucleic acid pellet is resuspended in 200 ul of 10 mM Tris-Cl pH 7.4, 0.1 mM EDTA, and 10 ug is digested with Kpn1 and BamH1, electrophoresed through 1.0% agarose, and transferred to nitrocellulose. Southern, *J. Mol. Biol.* 98:503 91975). Filters are hybridized overnight to CYP7 transgene specific probe in the presence of 10% dextran sulfate and washed twice in 2× SSC, 0.1% SDS at 64° C. A CYP7 transgene specific probe is a fragment of the CYP7 minigene that will not hybridize to related sequences in the host genome. This fragment is free of repetitive sequences. The CYP7 transgene specific probe is labeled with $^{32}$P dCTP by nick translation. Rigby et al., *J. Mol. Biol.* 113:237 (1977). Southern hybridization indicates cell lines contain the CYP7 minigene construct.

Transcription of the newly acquired gene in cultured cells is determined by extracting RNA from the cells and assaying the RNA by Northern Blot analysis, as described above.

Expression of recombinant human cholesterol 7α-hydroxylase in cell culture is evaluated by Western Blotting or immunocytochemistry. Alternatively, expression of a linked reporter gene, such as luciferase or LAC-Z, may be used to quantitate the tissues or cells expressing the transgene. For western blot or immunocytochemical detection of the recombinant protein, antibodies specific for human cholesterol 7α-hydroxylase are used to detect the presence of this enzyme in the various transformed cells.

In Vitro Agent Testing

Transformed cell lines of the invention are most useful as in vitro models for testing agents and procedures that promote or inhibit overexpression or under expression of CYP7. The CYP7 expressing cell lines are tested for materials that are suspected of promoting or inhibiting hypercholesterolemia. The cells are exposed to various dosages of a known agent and tested for the presence of human cholesterol 7α-hydroxylase.

What is claimed is:

1. A method of making a transgenic mouse that expresses human cholesterol 7α-hydroxylase (CYP7) in liver tissue in an amount higher than that of normal murine CYP7 expression in an unmodified, non-transgenic mouse comprising the steps of:
    (A) microinjecting a fertilized oocyte of a mouse with a human CYP7 minigene construct comprising a promoter region operably linked to CYP7 nucleotide fragments comprising exon I, intron I, exon II, intron II, exon III, exon IV, exon V, and exon VI, and
    (B) detecting expression of human cholesterol 7α-hydroxylase (CYP7) in liver tissue of a mouse generated from said fertilized oocyte.

2. A method according to claim 1, wherein said minigene construct further comprises a partial intron IV.

3. A method according to claim 2, wherein said minigene construct further comprises intron V.

4. A method according to claim 1, wherein said promoter region of said minigene construct is a promoter sequence obtained from a 5.5 kb sequenced fragment of λHG7α26 (ATCC 75534).

5. A transgenic mouse made by the method of claim 1 that expresses human cholesterol 7α-hydroxylase (CYP7) in liver tissue in an amount higher than that of normal murine CYP7 expression in an unmodified, non-transgenic mouse.

6. A progeny of the mouse of claim 5 that expresses human cholesterol 7α-hydroxylase (CYP7) in liver tissue in an amount higher than that of normal murine CYP7 expression in an unmodified, non-transgenic mouse.

7. A germ cell of the mouse of claim 5 that is capable of producing a transgenic mouse that expressed human cholesterol 7α-hydroxlase (CYP7) in liver tissue in an amount higher than that of normal murine CYP7 expression in an unmodified, non-transgenic mouse.

8. A transgenic mouse which expresses human cholesterol 7α-hydroxylase (CYP7), wherein said human CYP7 is expressed in liver tissue in an amount higher than that of normal murine CYP7 expression in an unmodified, non-transgenic mouse.

9. A progeny of the mouse of claim 8 that expresses human cholesterol 7α-hydroxylase (CYP7) in liver tissue in an amount higher than that of normal murine CYP7 expression in an unmodified, non-transgenic mouse.

10. A germ cell of the mouse of claim 8 that is capable of producing a transgenic mouse that expresses human cholesterol 7α-hydroxylase (CYP7) in liver tissue in an amount higher than that of normal murine CYP7 expression in an unmodified, non-transgenic mouse.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TACCGCTCGA GTGATTAGAA AGGGAAGGAT                              30

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAAGAATGAT AGATAAAAT                                        19

( 2 ) INFORMATION FOR SEQ ID NO:3:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Met Thr Thr Ser Leu Ile Trp Gly Ile Ala Ile Ala Ala Cys Cys
 1           5               10                  15

Cys Leu Trp Leu Ile Leu Gly Ile Arg Arg Arg Gln Thr Gly Glu Pro
            20              25                  30

Pro Leu Glu Asn Gly Leu Ile Pro Tyr Leu Gly Cys Ala Leu Gln Phe
        35              40              45

Gly Ala Asn Pro Leu Glu Phe Leu Arg Ala Asn Gln Arg Lys His Gly
    50              55              60

His Val Phe Thr Cys Lys Leu Met Gly Lys Tyr Val His Phe Ile Thr
65              70              75                  80

Asn Pro Leu Ser Tyr His Lys Val Leu Cys His Gly Lys Tyr Phe Asp
            85              90              95

Trp Lys Lys Phe His Phe Ala Thr Ser Ala Lys Ala Phe Gly His Arg
            100             105             110

Ser Ile Asp Pro Met Asp Gly Asn Thr Thr Glu Asn Ile Asn Asp Thr
        115             120             125

Phe Ile Lys Thr Leu Gln Gly His Ala Leu Asn Ser Leu Thr Glu Ser
    130             135             140

Met Met Glu Asn Leu Gln Arg Ile Met Arg Pro Pro Val Ser Ser Asn
145             150             155             160
```

|     |     |     |     |     |     |     |     |     |     |     |     |     |     |     |
|-----|-----|-----|-----|-----|-----|-----|-----|-----|-----|-----|-----|-----|-----|-----|
| Ser | Lys | Thr | Ala | Ala<br>165 | Trp | Val | Thr | Glu | Gly<br>170 | Met | Tyr | Ser | Phe | Cys<br>175 | Tyr |
| Arg | Val | Met | Phe<br>180 | Glu | Ala | Gly | Tyr | Leu<br>185 | Thr | Ile | Phe | Gly | Arg<br>190 | Asp | Leu |
| Thr | Arg | Arg<br>195 | Asp | Thr | Gln | Lys | Ala<br>200 | His | Ile | Leu | Asn | Asn<br>205 | Leu | Asp | Asn |
| Phe | Lys<br>210 | Gln | Phe | Asp | Lys | Val<br>215 | Phe | Pro | Ala | Leu | Val<br>220 | Ala | Gly | Leu | Pro |
| Ile<br>225 | His | Met | Phe | Arg | Thr<br>230 | Ala | His | Asn | Ala | Arg<br>235 | Glu | Lys | Leu | Ala | Glu<br>240 |
| Ser | Leu | Arg | His | Glu<br>245 | Asn | Leu | Gln | Lys | Arg<br>250 | Glu | Ser | Ile | Ser | Glu<br>255 | Leu |
| Ile | Ser | Leu | Arg<br>260 | Met | Phe | Leu | Asn | Asp<br>265 | Thr | Leu | Ser | Thr | Phe<br>270 | Asp | Asp |
| Leu | Glu | Lys<br>275 | Ala | Lys | Thr | His | Leu<br>280 | Val | Val | Leu | Trp | Ala<br>285 | Ser | Gln | Ala |
| Asn | Thr<br>290 | Ile | Pro | Ala | Thr | Phe<br>295 | Trp | Ser | Leu | Phe | Gln<br>300 | Met | Ile | Arg | Asn |
| Pro<br>305 | Glu | Ala | Met | Lys | Ala<br>310 | Ala | Thr | Glu | Glu | Val<br>315 | Lys | Arg | Thr | Leu | Glu<br>320 |
| Asn | Ala | Gly | Gln | Lys<br>325 | Val | Ser | Leu | Glu | Gly<br>330 | Asn | Pro | Ile | Cys | Leu<br>335 | Ser |
| Gln | Ala | Glu | Leu<br>340 | Asn | Asp | Leu | Pro | Val<br>345 | Leu | Asp | Ser | Ile | Ile<br>350 | Lys | Glu |
| Ser | Leu | Arg<br>355 | Leu | Ser | Ser | Ala | Ser<br>360 | Leu | Asn | Ile | Arg | Thr<br>365 | Ala | Lys | Glu |
| Asp | Phe<br>370 | Thr | Leu | His | Leu | Glu<br>375 | Asp | Gly | Ser | Tyr | Asn<br>380 | Ile | Arg | Lys | Asp |
| Asp<br>385 | Ile | Ile | Ala | Leu | Tyr<br>390 | Pro | Gln | Leu | Met | His<br>395 | Leu | Asp | Pro | Glu | Ile<br>400 |
| Tyr | Pro | Asp | Pro | Leu<br>405 | Thr | Phe | Lys | Tyr | Asp<br>410 | Arg | Tyr | Leu | Asp | Glu<br>415 | Asn |
| Gly | Lys | Thr | Lys<br>420 | Thr | Thr | Phe | Tyr | Cys<br>425 | Asn | Gly | Leu | Lys | Leu<br>430 | Lys | Tyr |
| Tyr | Tyr | Met<br>435 | Pro | Phe | Gly | Ser | Gly<br>440 | Ala | Thr | Ile | Cys | Pro<br>445 | Gly | Arg | Leu |
| Phe | Ala<br>450 | Ile | His | Glu | Ile | Lys<br>455 | Gln | Phe | Leu | Ile | Leu<br>460 | Met | Leu | Ser | Tyr |
| Phe<br>465 | Glu | Leu | Glu | Leu | Ile<br>470 | Glu | Gly | Gln | Ala | Lys<br>475 | Cys | Pro | Pro | Leu | Asp<br>480 |
| Gln | Ser | Arg | Ala | Gly<br>485 | Leu | Gly | Ile | Leu | Pro<br>490 | Pro | Leu | Asn | Asp | Ile<br>495 | Glu |
| Phe | Lys | Tyr | Lys<br>500 | Phe | Lys | His | Leu |     |     |     |     |     |     |     |     |

( 2 ) INFORMATION FOR SEQ ID NO:4:

( i ) SEQUENCE CHARACTERISTICS:
        ( A ) LENGTH: 5537 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TTTTGGTTA  TCTTTTCAGC  CGTGCCCCAC  TCTACTGGTA  CCAGTTTACT  GTATTAGTCG        60
```

-continued

| | | | | | |
|---|---|---|---|---|---|
| ATTTTCATGC | TGCTGATAAA | GACATACCTG | AAACTGGACA | ATTTACAAAA | GAAAGAGGTT | 120 |
| TATTGGACTT | ACAATTCTAC | ATCACTTGGG | AGGCCTCACA | ATCATGATGG | AAGGAGAAAG | 180 |
| GCACATCTCA | CATGGCAGCA | GACAAGAAAA | GAGCTTGTGC | AGGGAAACTC | CTCTTTTTAA | 240 |
| AACCATCAGA | TCTCATGAAA | TTTATTCATT | ATCATGACAA | TAGCACAGGA | AAGAACTGCA | 300 |
| CCCATAATTC | AGTCACCTCC | TACCAGGTTC | CTCCACAAC | ACGTGAGAAT | TCAAGATGAG | 360 |
| ATTTGGATGG | GGACACAGCC | AAACCATGTC | ACACTACCAT | GCCTGACTTC | CTTTCCATTT | 420 |
| TTGTATATTT | GCTTGTTCTT | CATTTGCCCG | AGAAGTAACT | CTAAAGGGCT | GTATTATTTG | 480 |
| GATATTAGAT | TGGCATTTTA | TCTGACTGGG | ATATCTTGCT | GTGATTGTCC | ATGTATAAGA | 540 |
| TCAGCTTTTC | TATAAGCCAT | ATTTTAAAA | AGATATATTA | ATTTTTAAA | AATCCACCTG | 600 |
| TCTAAATAAA | TGCACAAAGC | CCCCCAAAAA | CCTAGATTCT | AAGAAAAATC | TATGTACTGC | 660 |
| CATACAATGA | TTGATATTAA | TATTTATGGT | GATAAATTAC | ACACAAAAAA | TGTGTGATCT | 720 |
| CTGTTTAAAC | AGGCAAAAAC | AAAAAACACA | TGAAATAAAT | CTATGGCATC | TATAGCCAAA | 780 |
| ACTGGAAACA | ACCCACATAT | CCATCAATAG | GAAATCAGTT | AAATAAATTA | TAGTACATTT | 840 |
| ATCCAATGGA | AGATTAAGCA | CATATTCAAT | ATAATTATTT | ATACACACAT | ATAGATACAC | 900 |
| ACATGTATAA | ATATAGAGAA | TACTGTGGGT | GTATGTGTGT | GTGTGTTTAT | ATACATATAT | 960 |
| ATACACACAC | AGTACTGTTG | CCTACCTTCT | TTTGTCTTAA | TTCTGTGAAC | TCTCATTCAC | 1020 |
| TCTGCTTCAG | TAGGATACCT | CCTTCTTTTT | GGTTCTTAGA | CTCACCAAGT | TGATCCTTGA | 1080 |
| CTCAAGACAT | TGCATTTGCT | GCTTCCTCTT | CCTGGAATAT | CCTTCCTTCT | GATATTCACA | 1140 |
| TGAGTAGTCT | CTTCTTGTCA | TTCAGATCTC | AAATGTCACA | ATTTCAGAGA | GCCCATCTCT | 1200 |
| GATCATCATA | TCTAAAGTTG | TCCTCATTCC | CCCATAGCTT | TCTATACCAT | GTTTTATTTT | 1260 |
| TTTCATAACA | TGTATTTTAT | TACTCCTTTC | TCCATTGGAA | TAGAATCTCC | ATTAGATTAG | 1320 |
| GAAATCTGCC | TATCTTATTA | ATGCCTGCAA | CTGGAATACT | TTTGAAGAGT | TCTTGGCACG | 1380 |
| TAATAAATAC | TCAACTAATA | TTTTTGTGTA | CACAGAAATA | AAGTTTGGAA | GAACAGATGC | 1440 |
| CAAATTGTTA | CTAGTGGTTA | CTTCTGAGTA | AAGGAGTAGC | ATGGTAGGTA | AATTATTAAT | 1500 |
| AGATGTTCAC | TTTCCACCAA | GATATGTTTT | AGTTAGTCTT | AACTTACTTG | AAATGAAATT | 1560 |
| TATTACTTTA | ATAATTAGAA | ACATTGATAA | ACATTTTAGT | CACAAGAATG | ATAGATAAAA | 1620 |
| TTTTGATGCT | TCCAATAAGT | TATATTTATC | TAGAGGATGC | ACTTATGTAG | AATACTCTCT | 1680 |
| TGAGGATGTT | AGGTGAGTAA | CATGTTACTA | TATGTAGTAA | AATATCTATG | ATTTTATAAA | 1740 |
| AGCACTGAAA | CATGAAGCAG | CAGAAATGTT | TTTCCCAGTT | CTCTTTCCTC | TGAACTTGAT | 1800 |
| CACCGTCTCT | CTGGCAAAGC | ACCTAAATTA | ATTCTTCTTT | AAAAGTTAAC | AAGACCAAAT | 1860 |
| TATAAGCTTG | ATGAATAACT | CATTCTTATC | TTTCTTTAAA | TGATTATAGT | TTATGTATTT | 1920 |
| ATTAGCTATG | CCCATCTTAA | ACAGGTTTAT | TTGTTCTTTT | TACACATACC | AAACTCTTAA | 1980 |
| TATTAGCTGT | TGTCCCCAGG | TCCGAATGTT | AAGTCAACAT | ATATTTGAGA | GACCTTCAAC | 2040 |
| TTATCAAGTA | TTGCAGGTCT | CTGATTGCTT | TGGAACCACT | TCTGATACCT | GTGGACTTAG | 2100 |
| TTCAAGGCCA | GTTACTACCA | CTTTTTTTTT | TCTAATAGAA | TGAACAAATG | GCTAATTGTT | 2160 |
| TGCTTTGTCA | ACCAAGCTCA | AGTTAATGGA | TCTGGATACT | ATGTATATAA | AAAGCCTAGC | 2220 |
| TTGAGTCTCT | TTTCAGTGGC | ATCCTTCCCT | TTCTAATCAG | AGATTTCTT | CCTCAGAGAT | 2280 |
| TTGGCCTAG | ATTTGCAAAA | TGATGACCAC | ATCTTTGATT | TGGGGATTG | CTATAGCAGC | 2340 |
| ATGCTGTTGT | CTATGGCTTA | TTCTTGGAAT | TAGGAGAAGG | TAAGTAATGT | TTTATCTTTA | 2400 |
| AATTGCTCTT | TGATTCATCC | ATTTAATTTT | TTTACCTTCA | TTTTTATACA | GTAAATTTGG | 2460 |

-continued

| | | | | | |
|---|---|---|---|---|---|
| TTTTCTATAC | TTACACATAT | TAGCATTATC | TTCCTTATGT | TTAAATGAA | AAATTTGATT | 2520 |
| TGAATTTTTA | AAGTAATATC | TTTTTTACTA | TATCTCACAA | GACATATGAC | AGCTTCCCTT | 2580 |
| TTTAGTATTG | GCATATACCG | ATGGTAATAT | ATAAATGTAT | ATTGGTGTTA | AACATAACTG | 2640 |
| ACAGAAATTG | TATAAGGTCT | CTATGTACAT | TTATATGTGT | ATCTAAAGAG | GAAGCCCAGA | 2700 |
| TTAGTAAGGA | TACAAGTAGC | AAGTGGGAAT | CTACAATGGA | AAGGATTGCT | TTCTCTCACA | 2760 |
| TGGCTTCAAT | AGATACTCTT | GCTTAAATAA | ATGTTCTCTT | TTAAGCTCAT | TCTTGTGCAT | 2820 |
| CGCATAGACT | CAGCCTAAGC | CTGAACAAGA | GCATAGAGCC | TGAGCTGATC | ATTCTATTAC | 2880 |
| TGTTTTAAA | TAAATGTTAA | TCAACTGTGG | TGAATTGGGA | AAGTTTGCTG | AGTGTATGTG | 2940 |
| ACATCGATTT | CATTTATTTA | CAACTGGTTC | AAGAATGCAA | GAAAAACAAA | TACAGTCAGA | 3000 |
| TCCAGAACCA | TAGTTTATTT | AACTTCTAAT | TGGCTCAAGG | AGTAATTGTG | GGGAGGCATA | 3060 |
| TAGATATTCT | CTGCTATGTC | AATCTCAAAA | AGAGAAATA | ACCCTAACCA | TCTTTCAGCT | 3120 |
| TTGTAGATTG | CTATGTGTTT | TCTGCCTTTG | CAGTTTCTTT | CAGGCCTGAT | AGTTTTACT | 3180 |
| TTTAATTAAA | CTACTTATCT | TCAAACTAAG | AAAAGAAAGG | TAATTACTTT | ATACTGTATT | 3240 |
| ATTCTATCAA | GAGGTACAGA | AGTTTATGTT | GGAAAATAAG | TTTACATGTT | CTAATAAAAA | 3300 |
| CATTTTAAAG | GAGCACTGAA | TTACAATAGA | TGATTCCGTC | AGTGTTTATC | TTACTCAATT | 3360 |
| TCATTTTATA | ATAAGCTGAT | TTCTCACATG | AGATTCTTCT | TCTCTGAAAC | CATCCTTATA | 3420 |
| GAATATAATA | TAGATATCTT | TAAACTAGGA | ATATTTCAA | AACCTCAGTT | CTGAAATCCT | 3480 |
| CCCTTATTCA | GTGATCTGTG | TCTTTAAAGA | AAATAATCAA | AAGAAACATT | TTGAGATATT | 3540 |
| TAGAAAAATG | ATGCTTAGCA | AAGTGATAAA | CACTAGAATG | TAGTTTTGTT | TCCGCACTGA | 3600 |
| CAACAAGAAT | CTTGTTGGTC | TTGTAAATCC | TTTTGCCTGT | ATCACTGGGA | AAAGTGATGA | 3660 |
| GCACATAGTA | GACGGGTGCT | TGTTGAATGT | GTATATGGAC | GGATGCATGA | ATGGATGGAT | 3720 |
| TTAGTAATCC | TTTCCACCAA | CATATCATGT | TACTAGGTTA | ATATAACCTA | TTACTGTAGT | 3780 |
| AAAAGAGCAG | GGCCCATCCA | ACAAAAGAAA | TATCTATAAA | CTATAGGGTT | TCAAAGTTTG | 3840 |
| AAGTCAGTGG | GAAAAATTTT | AAAACCTGAT | GTAAGTAAAA | ACCCAAAACT | GTAATCATCC | 3900 |
| ATGTCTATCA | TACACTTGTG | TCTGACAGGC | AAACGGGTGA | ACCACCTCTA | GAGAATGGAT | 3960 |
| TAATTCCATA | CCTGGGCTGT | GCTCTGCAAT | TTGGTGCCAA | TCCTCTTGAG | TTCCTCAGAG | 4020 |
| CAAATCAAAG | GAAACATGGT | CATGTTTTTA | CCTGCAAACT | AATGGGAAAA | TATGTCCATT | 4080 |
| TCATCACAAA | TCCCTTGTCA | TACCATAAGG | TGTTGTGCCA | CGGAAAATAT | TTTGATTGGA | 4140 |
| AAAAATTTCA | CTTTGCTACT | TCTGCGAAGG | TAAGCAGTTT | TACATTTATA | TACCATTCTG | 4200 |
| TTTGTCTTCT | ACCTTTTTAT | GTGCTTGTCT | ATTTAGAAAT | TTTGATGTAC | TTAGATTTTA | 4260 |
| TGATAAAGGT | GTTGAAGAGA | GTTATCCTTA | TGTGGAGATT | CTTAGAAACA | TAAATAAATT | 4320 |
| ATACGTAGCT | TCTTAGTAAT | AATCATTTAG | AAAGTCAAAA | TAGGTATAGA | TTTCCGTCAT | 4380 |
| TTGCTTTGCA | CGAGCTAATG | AGGGTGAAAT | ACAGATTAAA | TGCTCTACTG | AGACAGGTGG | 4440 |
| CACTGTACGA | ATAAGATAGA | TTAAAATTCA | TCACATCAGC | AATGTCTATG | CAGAGCGAAG | 4500 |
| TGACGGAAAC | CTAACATTCA | GCAGTTGTCT | CACCACACTT | GTGCCACACA | GTGTTTCATT | 4560 |
| TTGATAAGGA | ATTGGCAAGA | TATTTTAACA | TCATTTAGAT | GTAATAAAAG | AAGATCTGTT | 4620 |
| ACTGAGAAAA | AAAACCAATA | ACTACTTACT | TACTGCAAAT | AAATATTAGC | TTTGGTCTTT | 4680 |
| GTGACTAAGT | AGCTTAAAGT | TTGGTTAAAA | TACATCTACA | GCTGGACACA | ATGGAACACA | 4740 |
| CCTGTAGTCC | CTGCTATTTG | AGAGGCTGAG | GCAGGAGGAT | CGCTTGAGTC | CAGGAGTTTG | 4800 |
| AGGCTGCAGT | GAGCTATCAT | TGTGTCACTG | CACTCCAGCC | TGGGTGACAA | TGTGAGACCC | 4860 |

| | | | | | |
|---|---|---|---|---|---|
| CATCTCTAAA | AGAAAAAGAA | AAAGAAATCT | ACAAATAATA | TAAAAGATAA | CTAATGATTT | 4920 |
| TAAAACATTA | TCAATTAGTT | TATGTGCAAT | AGCTGTAAAT | AAGTGCAGTA | GCATAAGAAA | 4980 |
| TAAGACATAG | ATGACTTGAG | TGATCCAGGG | GAGTGCCACT | GAAGTTGGCT | TTAAAGGAAA | 5040 |
| GGTACAGTTT | GGTCATTTAT | TTGTAAAGTG | CTATGAACTT | GTACAAGGGA | AAGCCAATTT | 5100 |
| CCCGTGTTTA | CCAAGTAAGG | AACTATGAAA | GTATCTAATC | CGTTTTCAG | TCATTTACTA | 5160 |
| TGACTAGGTC | AGGTTTAACT | TCTTTTTCTG | CATGTTTTAT | TTGCTATCAG | GCATTTGGGC | 5220 |
| ACAGAAGCAT | TGACCCGATG | GATGGAAATA | CCACTGAAAA | CATAAACGAC | ACTTTCATCA | 5280 |
| AAACCCTGCA | GGGCCATGCC | TTGAATTCCC | TCACGGAAAG | CATGATGGAA | AACCTCCAAC | 5340 |
| GTATCATGAG | ACCTCCAGTC | TCCTCTAACT | CAAAGACCGC | TGCCTGGGTG | ACAGAAGGGA | 5400 |
| TGTATTCTTT | CTGCTACCGA | GTGATGTTTG | AAGCTGGGTA | TTTAACTATC | TTTGGCAGAG | 5460 |
| ATCTTACAAG | GCGGGACACA | CAGAAAGCAC | ATATTCTAAA | CAATCTTGAC | AACTTCAAGC | 5520 |
| AATTCGACAA | AGTCTTT | | | | | 5537 |

( 2 ) INFORMATION FOR SEQ ID NO:5:

( i ) SEQUENCE CHARACTERISTICS:
        ( A ) LENGTH: 2575 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| GAATTCTACT | CTTTAAAGGG | GTGAATATTA | TGGTACTTGA | ATTTTATCTC | AAGAAAAATG | 60 |
| AATAAAAAGT | AACTAAATCA | TTGAAAATAT | CTGATGGCAT | GGGGTTTGTG | GGGTAACTGG | 120 |
| CATTCCACAG | TGATTTTCAA | AGGGCTTGTG | CTGTTTCAT | TTGCTTTGT | TTAGTTATG | 180 |
| GAGCCCTTCC | TTGAAACAAA | CTTCATACTA | CAGTCCTCTT | TCATGAAGCA | GAAGAGGGCA | 240 |
| GTGGGCAGAG | CTCTCCTTTG | GCTTTCTCCC | CCACCACAAC | AGGGAGCCCT | GGAGCTCTAG | 300 |
| GAGAGAAAAT | CTGAAATATA | AAGGGCATGC | ATGTGAGCTG | TGGAGTCCCA | GAGCCCTGGG | 360 |
| TTTGCATCCT | AGATCTGCAA | CTCCCGTGAA | TTGAGTTTTG | GGAAGTTGCT | GAAACTCTGA | 420 |
| CCTCCTGTTT | TCTCATGGTA | TTGTTGTAAG | GGTTAAATGA | GACAATGTAT | GTGAAGACCC | 480 |
| TGGCCCCACA | GTAGAGGCTC | TGCACACATT | TCAGCGATAC | TTTCCTCATG | TATTTCCAAA | 540 |
| AATGTTTTCT | CATTTTCTTA | AAATGTCAGA | AAGAAGACAA | CAGAACTTAC | TTGCCTTTTA | 600 |
| CAACAGAACA | AATGGAGCAA | GTCAGAGGTC | AAGGTGCTAA | CATTCTTCAT | GGTTCCTCAC | 660 |
| CACCTTTTGT | TCTGTTAGCC | TATAGGGAAA | AGTCTTCTTT | CTCATCTCAT | TATCTGCAGG | 720 |
| GGAAAATAGT | ACTTCAGCAA | GTGATCCAGT | TGAAGAACAT | CTCCAGGGCC | ATTAACATAC | 780 |
| AGAGGTTTGT | TCTACTCTCT | CTGTGCTCCA | TGTCTAAGAA | CCTCAGCCTT | CCTCCTAGGA | 840 |
| GCTAGGGAAA | GTCAGGAAAG | TGAAAATAGT | ACCCCAGCTA | ATGAACTGCC | CTGTGCTGGC | 900 |
| CTGAGAAGAC | AAGACCAGCT | TCCTCAATGG | CTCAAGATTT | GGTTTCCTTC | AATATGTCCT | 960 |
| TTTGGAAATA | TGTCCATGAC | ATCGGAGAGA | TAAAGGAGC | CAGGATTGCT | CACATTCAGG | 1020 |
| AAAAAAGCTC | CACTATCTTT | CTCTCTCTCC | CTCTTTCTCT | CCCTCCCCCT | GACTGCCCTC | 1080 |
| TTCTCTATCT | CTCTCTCTCC | CTGAGCTGGC | AAGGTTAATT | GGTCGCAGAA | AGCCGAAGAA | 1140 |
| ACAAGTGGGC | CTCCTGGAAC | AAAGTTCAAA | AAGCCGAAAA | CGGGAAGAAA | ACTAACCACA | 1200 |
| AAAGTAAAGG | AACCACTTAG | CCTTCTTTGA | TTCCAGGCCC | CCAAGCCTGT | CTTTAACTTG | 1260 |

-continued

| | | | | | |
|---|---|---|---|---|---|
| GATGAATGGA | GTTCTTCCTG | TGCTACAGCA | CCGCATAGTA | GGGGCTGCCC | TGGGCCTGAA | 1320 |
| GCCAGAGCTT | CACCATATTC | AGTCATCTGT | ACATTGAGGC | AACAGTGCCT | GCTTCATGGT | 1380 |
| GCTACCCTGT | GGATTAAATG | AAGCAAGTTT | TTGATGATCT | TGACACTGAA | TATTGATGCA | 1440 |
| TTGGTCAGAC | TTTTCTGAT | AGTAAAAAAT | GGTGGTTTCT | TGTTGTCAGA | AATCAAATCA | 1500 |
| ATATATTTGT | TCTCCTGTTG | ATTAGCTATG | TCCCCTAGAG | GGCAGCGACT | TTGCCTGTCT | 1560 |
| TATTTATCTC | TGCATCTCCA | GCACTTAAAA | GGTGCCTTGC | ATAAGGTACA | TATTAAGTTC | 1620 |
| ATATGAATGA | ATGAATGAAA | TGCATATGAT | TTATTCATAC | CCAGTTGGTG | GTGTGTTTAC | 1680 |
| CCTTTCCTAA | ACCTGTAGTC | AGATGGCCTT | TGAATCCCCT | GTACTTCTTG | TGAGGTACTG | 1740 |
| TGCTGTAAAG | GTGGACTATC | ACACTTCAGT | TCAGAGCAAT | CTGGGCTTGA | ATCCTGGATT | 1800 |
| TGCCAGTTTA | TTAACTATAG | CAAACATTTT | TGAGCATACA | TTGTGCCAAG | TGCTAGGCTA | 1860 |
| ACTGTCTTAC | ACACATTGTC | TTATTTCGTC | TTAATATCTA | TGAGTCATGC | ACTATAATCA | 1920 |
| TCCCCATTTT | ACAGATAAGA | AAGCAAAGAC | TGGAGAGGA | AAAGCATCTT | GTTCAAAGGT | 1980 |
| AAATACTTAA | TGGCCAAGCC | AACATGCAAA | TCTAGATTTA | ATTGCAGCTT | CCTCTTCATC | 2040 |
| TACCATTCGA | ACTAATTCAA | GCTATGTAAT | ATTTCCCACT | GAACCTTCTT | GCCTCTACTT | 2100 |
| CCTCATCTTT | AACATGGTCA | AAATACCTGT | CCTGCCCAAG | TTAGTTATTT | CATTAAAGTA | 2160 |
| GAAAAATACA | AGAGAAGCTT | TTAAAATGTG | AAACCTCAAA | TGAATGTAAA | ATTATGATGA | 2220 |
| TTCCTTTAGA | ATTTGTCAAC | ACCTTCTTTT | CTCTACTCCT | GCTAGGCATT | TACAATCTCA | 2280 |
| AAACCATGTA | TTTAAGATGC | AAAACTATAT | TTGTATTTGC | CATAACTGGT | TTCTTTCCCT | 2340 |
| ATGGCTTCAT | GAAAATGTGG | CTCGAATGTG | TTTATTATGA | AAGCCCCAAA | TTAATCACGA | 2400 |
| CAAGACTTCA | CCAGCCCATT | CCACAATAGA | CTCCCATTAC | TTTGCCCTGA | CTTAGAAACC | 2460 |
| TCATATACAG | TCTTGATTCA | GTACAGCTCT | GTGATGCTCT | TGGAAAATGC | AAAGTGCTTT | 2520 |
| CTTAATTGAG | GCAATCTGTG | TCCCACTACA | GAGAGGTGGT | TTAACTTGTG | AATTC | 2575 |

( 2 ) INFORMATION FOR SEQ ID NO:6:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| AGAGCAACCT | GGGCAACATA | GCAAAACCCT | GTCTCTGCAA | ACAATAAAAA | GAAGAAAATT | 60 |
| AGCTGGGTAT | GGTGGCACAT | GCTATAGTCG | CAGCTACTCG | AGAGGTTGAG | GTGGGAGGAT | 120 |
| CAGTTCAGCC | TGGGAGGTTG | AGGCTGCAGT | GAGCCAGATC | ATGCCACTGC | ACTGCAGCAT | 180 |
| GGGCAACAGA | ATGAGACCCT | GGCTAAAAGA | AAACAAAATA | AAAAATTCAG | ACACAGGTTG | 240 |
| AATCATTGAT | AACAGCATAG | TGGTAACAGA | AAGAAAGTTT | GGGAAATTTT | TATCTGATCA | 300 |
| GCTTCCCATA | CCCTGTTCAT | CTTTGTGTTA | TGCACTGCCA | GGCTGTCTGT | AGGTTCAGAC | 360 |
| TCTATATCAT | ATGACCTTCA | AACACTTGGT | TTGTTCTTCT | CCTTCCTTCC | TCCCTTCTTC | 420 |
| TTTCATTTTT | TATCTTTTTT | TCTTTTAAAA | TGTTTAGATA | GTATAATAAG | GAACTGCTGA | 480 |
| GGCTTTCCAG | TGCCTCCCTC | AACATCCGGA | CAGCTAAGGA | GGATTTCACT | TTGCACCTTG | 540 |
| AGGACGGTTC | CTACAACATC | CGAAAGATG | ACATCATAGC | TCTTTACCCA | CAGTTAATGC | 600 |
| ACTTAGATCC | AGAAATCTAC | CCAGACCCTT | TGGTAAAGTC | GCAGTGTGCC | CGAATTGAAA | 660 |
| TTCAATATCC | AGGTGATAGC | TACCTAGATC | TAAATAAAGA | GGAAATTTAC | AATGGTAGAA | 720 |

```
TTGATTTTCT CATAGTAGTC ACAGGAATTG TCTGACTTAA TTGTGTTAAA TATTCATATA      780
TTTTGGAAAA TTTAGATAGT GGTCTGAATT TTTCATTTTA GTCCTGATAT TTGCCATCAC      840
ACAGTCTTTG CTAGATTATA TTTGCAGTCA TGATAATAAA CCTGCCACTT TTTTTTTCTT      900
AAAAAGCACC TCCTCCCAAA TCCAGGAAAT TGGAGGCTAA TATATTGATT ATTCTAGTTT      960
CTTCTGGGAA CCCTTCTCTC TCTAGCTCTG CCTGACTAAG GAACTAATCG TTCAAGCAGG     1020
ATAGGAAGGT ATCACAAGGC TTCCTTAGCT GCATTAAGCT CCTGTTCCTT ATTACTTTCT     1080
GATTCAATGT GGAGTATTTG CTAAATCACT AATGGGGTAG AATTAAAAAG AAAATTACTC     1140
TTTGGAGCTT CCAGGTTTAG AAAGAGATAA ATTTCTTTAA AACTAGCTTA AAGGCGGTTT     1200
TCTTTGTATT TTTATTGCAG ACTTTTAAAT ATGATAGGTA TCTTGATGAA AACGGGAAGA     1260
CAAAGACTAC CTTCTATTGT AATGGACTCA AGTAAAGTA TTACTACATG CCCTTTGGAT      1320
CGGGAGCTAC AATATGTCCT GGAAGATTGT TCGCTATCCA CGAAATCAAG CAATTTTTGA     1380
TTCTGATGCT TTCTTATTTT GAATTGGAGC TTATAGAGGG CCAAGCTAAA TGTCCACCTT     1440
TGGACCAGTC CCGGGCAGGC TTGGGCATTT TGCCGCCATT GAATGATATT GAATTTAAAT     1500
ATAAATTCAA GCATTTGTGA ATACATGGCT GGAATAAGAG GACACTAGAT ATTACAGGAC     1560
TGCAGAACAC CCTCACCACA CAGTCCCTTT GGACAAATGC ATTTAGTGGT GGCACCACAC     1620
AGTCCCTTTG GACAAATGCA TTTAGTGGTG GTAGAAATGA TTCACCAGGT CCAATGTTGT     1680
TCACCAGTGC TTGCTTGTGA AATCTTAACA TTTGGTGAC AGTTCCAGA TGCTATCACA       1740
GACTCTGCTA GTGAAAAGAA CTAGTTTCTA GGAGCACAAT AATTTGTTTT CATTTGTATA     1800
AGTCCATGAA TGTTCATATA GCCAGGGATT GAAGTTTATT ATTTCAAAG GAAAACACCT      1860
TTATTTTATT TTTTTTCAAA ATGAAGATAC ACATTACAGC CAGGTGTGGT AGCAGGCACC     1920
TGTAGTCTTA GCTACTCGAG AGGCCAAAGA AGGAGGATGC TTGAGCCCAG GAGTTCAAGA     1980
CCAGCCTGGA CAGCTTAGTG AGATCCCGTC TCCAAAGAAA AGATATGTAT TCTAATTGGC     2040
AGATTGTTTT TTCCTAAGGA AACTGCTTTA TTTTTATAAA ACTGCCTGAC AATTATGAAA     2100
AAATGTTCAA ATTCACGTTC TAGTGAAACT GCATTATTTG TTGACTAGAT GGTGGGGTTC     2160
TTCGGGTGTG ATCATATATC ATAAAGGATA TTTCAAATGT TATGATTAGT TATGTCTTTT     2220
AATAAAAAGG AAATATTTTT CAACTTCTTC TATATCCAAA ATTCAGGGCT TTAAACATGA     2280
TTATCTTGAT TTCCCAAAAA CACTAAAGGT GGTTTT                              2316
```